(12) United States Patent
Li

(10) Patent No.: US 12,257,227 B2
(45) Date of Patent: Mar. 25, 2025

(54) COMBINATION SOLUTION FOR TREATING CHEMOTHERAPY REFRACTORY CANCER

(71) Applicant: 1GLOBE BIOMEDICAL CO., LTD., Beijing (CN)

(72) Inventor: Chiang J. Li, Cambridge, MA (US)

(73) Assignee: 1GLOBE BIOMEDICAL CO., LTD., Beijing (CN)

( * ) Notice: Subject to any disclaimer, the term of this patent is extended or adjusted under 35 U.S.C. 154(b) by 628 days.

(21) Appl. No.: 17/284,654

(22) PCT Filed: Oct. 12, 2019

(86) PCT No.: PCT/CN2019/110904
§ 371 (c)(1),
(2) Date: Apr. 12, 2021

(87) PCT Pub. No.: WO2020/074010
PCT Pub. Date: Apr. 16, 2020

(65) Prior Publication Data
US 2021/0393571 A1    Dec. 23, 2021

(30) Foreign Application Priority Data
Oct. 12, 2018 (CN) ......................... 201811195239.3

(51) Int. Cl.
*A61K 31/343* (2006.01)
*A61K 31/337* (2006.01)
*A61K 31/7068* (2006.01)
*A61P 35/00* (2006.01)

(52) U.S. Cl.
CPC .......... *A61K 31/343* (2013.01); *A61K 31/337* (2013.01); *A61K 31/7068* (2013.01); *A61P 35/00* (2018.01)

(58) Field of Classification Search
CPC ............... A61K 31/343; A61K 31/337; A61K 31/7068; A61K 2300/00; A61P 35/00
See application file for complete search history.

(56) References Cited

U.S. PATENT DOCUMENTS

| 9,150,530 | B2 | 10/2015 | Jiang et al. |
| 9,745,278 | B2 | 8/2017 | Li et al. |
| 2016/0030384 | A1 | 2/2016 | Li et al. |
| 2018/0085341 | A1 | 3/2018 | Li et al. |

FOREIGN PATENT DOCUMENTS

| WO | 2009/036101 A1 | 3/2009 |
| WO | 2009036059 A2 | 3/2009 |
| WO | 2011116398 A1 | 9/2011 |
| WO | 2011116399 A1 | 9/2011 |
| WO | 2013166618 A1 | 11/2013 |
| WO | 2014/169078 A2 | 10/2014 |
| WO | 2017132049 A1 | 8/2017 |

OTHER PUBLICATIONS

Hubbard et al., Drugs, 2017, 77, p. 1091-1103. (Year: 2017).*
Stinchcombe, T.E., Nanomedicine, 2007, 2(4), p. 415-423, abstract only. (Year: 2007).*
Ma et al., Clin. Cancer Res., 2013, 19(20). p. 5572-5579. (Year: 2013).*
ISA(CN), International Search Report for PCT/CN2019/110904, Jan. 10, 2020, China.
Sonbol, M. et al., "CanStem111P trial : a Phase III study of napabucasin plus nab-paclitaxel with gemcitabine," Future Oncology, Feb. 15, 2019, 12:15, 1295-1302.
Boman, B. M., et al. "Human Colon Cancer Stem Cells: A New Paradigm in Human Gastrointestinal Oncology," J. Clin. Oncol. 2008. 26(17): p. 2795-99.
Gupta, PB et al., "Cancer Stem Cells: mirage or reality?" Nat. Med. 2009; 15(9): 1010-1012.
Clarke, MF, "Self-renewal and Solid Tumor Stem Cell," Biol. Blood Marrow Transplant. 2009; 11 (2 suppl 2): 14-16.
Jordan, CT et al. "Cancer Stem Cells" N. Engl. J. Med. 2006; 355(12)1253-1261.
Boman, B. M., et al. "Cancer Stem Cells: A Step Toward the Cure" J. Clin. Oncol. 2008. 26(17) p. 2795-99.
Catlett-Falcone, R., et al. "Constitutive Activation of Stat3 Signaling Confers Resistance to Apoptosis in Human J266 Myeloma Cells" Immunity, 1999. 10(1), p. 105-15.
Bromberg, J. F., et al. "Stat3 as an Oncogene" Cell, 1999. 98(3), p. 295-303.
Kanda, N., et al. "STAT3 is constitutively activated and supports cell survival in association with survivin expression in gastric cancer cells" Oncogene, 2004. 23(28) p. 4921-29.
Schlette, E. J., et al. "Survivin Expression Predicts Poorer Prognosis in Anaplastic Large-Cell Lymphoma" J Clin Oncol, 2004. 22(9) p. 1682-88.
Niu, G., et al. "Constitutive Stat3 activity up-regulates VEGF expression and tumor angiogenesis" Oncogene, 2002. 21 (13) p. 2000-08.

(Continued)

*Primary Examiner* — Jonathan S Lau
(74) *Attorney, Agent, or Firm* — Milstein Zhang & Wu LLC; Duan Wu, Esq.

(57) ABSTRACT

The use of a pharmaceutical composition in treating cancer in a subject comprising a therapeutically effective amount of a compound of formula (I), a therapeutically effective amount of paclitaxel and a low dose of gemcitabine, and a kit included above composition thereof.

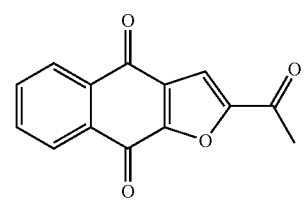

(I)

21 Claims, 5 Drawing Sheets

(56) References Cited

OTHER PUBLICATIONS

Xie, T. X., et al. "Stat3 activation regulates the expression of matrix metalloproteinase-2 and tumor invasion and metastasis" Oncogene, 2004. 23(20) p. 3550-60.

Furqan, et al. "STAT inhibitors for cancer therapy" Journal of Hematology & Oncology (2013) 6:90.

Kortylewski, M., et al. "Inhibiting Stat3 signaling in the hematopoietic system elicits multicomponent antitumor immunity" Nat. Med., 2005. 11(12), p. 1314-21.

Burdelya, L., et al. "Stat3 Activity in Melanoma Cells Affects Migration of Immune Effector Cells and Nitric Oxide-Mediated Antitumor Effects" J. Immunol., 2005. 174(7), p. 3925-31.

Wang, T., et al. "Regulation of the innate and adaptive immune responses by Stat-3 signaling in tumor cells" Nat. Med., 2004, 10(1), p. 48-54.

Lin et al., "STAT signaling in the pathogenesis and treatment of leukemias" Oncogene (2000) 19, 2496-2504.

Bromberg, J. "Stat proteins and oncogenesis" J. Clin. Invest. (2002) 109:1139-1142.

Buettner et al., "Activated STAT Signaling in Human Tumors Provides Novel Molecular Targets for Therapeutic Intervention" Clinical Cancer Research (2002) 8, 945-954.

Frank, D., "STAT3 as a central mediator of neoplastic cellular transformation" Cancer Letters 251 (2007) 199-210.

Yu, et al. "The Stats of Cancer—New Molecular Targets Come of Age" Nature Reviews Cancer (2004) 4, 97-105.

Pedranzini, L., et al. "Stat3 is required for the development of skin cancer" J Clin. Invest., 2004. 114(5), p. 619-22.

Darnell, J. E. "Validating Stat3 in cancer therapy" Nat. Med., 2005. 11(6), p. 595-96.

Zhang, L., et al. "Intratumoral Delivery and Suppression of Prostate Tumor Growth by Attenuated *Salmonella enterica serovar typhimurium* Carrying Plasmid-Based Small Interfering RNAs" Cancer Res, 2007. 67(12), p. 5859-64.

Libby, P. et al. "Inflammation and Atherosclerosis" Circulation, 2002. 105(9), p. 1135-43.

Stephens, J. W., et al. "A common functional variant in the interleukin-6 gene is associated with increased body mass index in subjects with type 2 diabetes mellitus" Mol. Genet. Metab., 2004. 82(2), p. 180-86.

Cesari, M., et al. "Inflammatory Markers and Onset of Cardiovascular Events Results From the Health ABC Study" Circulation, 2003. 108(19), p. 2317-22.

Orshal, J. M. and R. A. Khalil. "Interleukin-6 impairs endothelium-dependent NO-CGMP-mediated relaxation and enhances contraction in systemic vessels of pregnant rats" Am. J. Physiol. Regul. Integr. Comp. Physiol., 2004, 286 (6), p. R1013-23.

Manolagas, S. C. "Role of Cytokines in Bone Resorption" Bone, 1995. 17(2 Suppl), p. 63S-67S.

Yaffe, K. et al., "Inflammatory markers and cognition in well-functioning African-American and white elders" Neurology, 2003. 61(1), p. 76-80.

Wei, D. et al., "Stat3 activation regulates the expression of vascular endothelial growth factor and human pancreatic cancer angiogenesis and metastasis" Oncogene (2003) 22(3), 319-329.

Scholz, A. et al. "Activated Signal Transducer and Activator of Transcription 3 (STAT3) Supports the Malignant Phenotype of Human Pancreatic Cancer" Gastroenterology (2003) 125, 891-905.

Toyonaga, T. et al. "Blockade of constitutively activated Janus kinase/signal transducer and activator of transcription-3 pathway inhibits growth of human pancreatic cancer" Cancer Lett. (2003) 10;201(1), 107-116.

Qiu, Z. et al. "RNA interference-mediated signal transducers and activators of transcription 3 gene silencing inhibits Invasion and metastasis of human pancreatic cancer cells" Cancer Sci. (2007) 98(7), 1099-1106.

Bonnet, D. and J. E. Dick. "Human acute myelid leukemia is organized as a hierarchy that orginates from a primitive hematopoietic cell" Nat. Med., 1997. 3(7), p. 730-37.

Hambardzumyan, D. et al. "Radiation resistance and stem-like cells in brain tumors" Cancer Cell, 2006. 10(6), p. 454-56.

Baumann, M., et al. Nat. "Exploring the role of cancer stem cells in radioresistance" Rev. Cancer, 2008. 8(7), p. 545-54.

Jones, RJ et al., "Cancer Stem Cells: Are We Missing the Target?" J Natl Cancer Inst. 2004; 96(8), 583-585.

Berge, S. J. et al., "Pharmaceutical Salts" Pharmaceutical Sciences, 1977, 66: 1-19.

Alembic Pharmaceutical, Inc. (NJ, USA) Drug label of paclitaxel injection,: Feb. 2022, published by National Library of Medicine at NIH.

Drug Bank Online,"Paclitaxel: Uses, Interactions, Mechanism of Action" published online at https://go.drugbank.com/drugs/DB01229.

National Cancer Institute "Pancreatic Cancer Treatment (PDQ®)—HealthProfessional Version" Oct. 2023 at https://www.cancer.gov/types/pancreatic/hp/pancreatic-treatment-pdq#_2067.

Mahtani RL et al. "Comparative effectiveness of early-line nab-paclitaxel vs. paclitaxel in patients with metastatic breast cancer . . . " Cancer Manag Res. 2018:10 249-256.

European Society for Medical Oncology (ESMO), "ema-reminds-physicians-to-use-atezolizumab-with-nab-paclitax" Oct. 2022, published online at www.esmo.org.oncology-news/.

Schmid, P. et al "IMpassion130: Results from a global, randomised, double-blind, phase III study of atezolizumab (atezo) . . . " Oct. 2018, ESMO Annals of Oncol 29:Supp 8.

Miles, D. et al. "Primary results from IMpassion131 . . . " Jul. 2021, ESMO Annals of Oncol, 32:8, 994-1004.

Sumitomo Pharma "A study of BBI608 Administered With Paclitaxel in Adult Patients with Advanced Malignancies" NCT01325441 online 2023 at ClinicalTrials.gov.

Sumitomo Pharma"A Study of BBI608 Plus Weekly Paclitaxel to Treat Gastric and Gastro-Esophageal Junction Cancer (Brighter)" NCT02178956 online 2023 at ClinicalTrials.gov.

Shah, M. et al. "The Brighter trial: A phase 3 randomizeddouble-blind study of napabucasin (NAPA)plus paclitaxel (PTX) . . . " Jun. 2018, J Clinical Oncology 36: 15_suppl 4010.

El-Rayes, B. F. et al. "A phase Ib extension studyof cancer stemness inhibitorBB608 (napabucasin) incombination withgemcitabine . . . " 2016, J Clinical Oncol 34:15_supp 4128.

Sumitomo Pharma "A Study of BBI608 in Combination With Standard Chemotherapies in AdultPatients With Pancreatic Cancer" NCT02231723 online 2023 at ClinicalTrials.gov.

Sumitomo Pharma "A Study of Napabucasin Plus Nab-Paclitaxel With Gemcitabine in AdultPatients With Metastatic Pancreatic Adenocarcinoma . . . " online 2023 at ClinicalTrials.gov.

IP Australia, Australian Patent Application No. 2019357933 (equivalent to presnt filing), Examination report No. 1 mailed Nov. 18, 2022.

IP Australia, Notice of Acceptance in Australian Patent Application No. 2019357933, Nov. 8, 2023.

Bekaii-Saab, T. et al., "CanStem111P trial A Phase 3 Study" Annals of Oncology, Jun. 1, 2018, vol. 29, Supplement 5, V51-V52.

Brazilian Patent Office, Office action in Brazilian Patent Application No. BR1120210068988 (equivalent to presnt filing), mailed Sep. 19, 2023—Portuguese original.

Brazilian Patent Office, Office action in Brazilian Patent Application No. BR1120210068988 (equivalent to presnt filing), mailed Sep. 19, 2023—English translation.

Chinese Patent Office, Search Report in equivalent Chinese applictaion No. 201980066957.7, mailed May 26, 2023.

Chinese Patent Office, Office action in equivalent Chinses applictaion No. 201980066957.7, mailed May 31, 2023.

Euroasian Patent Office, office action in equivalent Eurasian Patent Application No. 202190771, mailed Sep. 28, 2022 in Russian original.

Euroasian Patent Office, office action in equivalent Eurasian Patent Application No. 202190771, mailed Sep. 28, 2022 in English translation.

Euroasian Patent Office, Notification on readiness to grant a Eurasian Patent in equivalent Eurasian Patent Application No. 202190771, Aug. 28, 2023 in Russian.

(56) References Cited

OTHER PUBLICATIONS

Euroasian Patent Office, Notification on readiness to grant a Eurasian Patent in equivalent Eurasian Patent Application No. 202190771, Aug. 28, 2023 in English.
European Patent Office, Extended European Search Report in equivalent European patent application No. 19871382.8, Jun. 2022 in English.
Indonesian Patent Office, Office action in equivalent Indonesian Application No. P00202102821, mailed Dec. 13, 2022.
Isralei Patent Office, Office action in equivalent Israel Patent Application No. 282228, mailed Nov. 28, 2023, in English.
Japanese Patent Office, Office action in eqJapanese Patent Application No. 2021-520113, including cited reference, mailed Sep. 19, 2023.
Sakamoto, H. et al, "Comparison of standard-dose and low-dose gemcitabine regimens in pancreatic adenocarcinoma patients" Journal of Gastroenterology, 2006, 4170-76.
Mexican Patent Office, Office action in equivalent Mexican Patent Application.MXa2021004151, mailed Nov. 17, 2023.
Singaporean Patent Office, office action in equivalent Singapore Patent Application No. 11202103707T, the first Wirtten Opinion mailed Oct. 5, 2022.
Taiwan Patent Office, office action in equivalent Taiwan Patent application No. 108136944, Jul. 5, 2023.
Vietnamese Patent Office, office action in equivalent Vietnamese Patent Application No. 1-2021-02660, mailed Oct. 31, 2023 in Vietnamese Original.
Vietnamese Patent Office, office action in equivalent Vietnamese Patent Application No. 1-2021-02660, mailed Oct. 31, 2023 in English.
Vaz, J. et al., "SPARC: A Potential Prognostic and Therapeutic Target in Pancreatic Cancer" Pancreas 2015; 44:1024-1035.
Abraxis BioScience, LLC, "Abraxane(R) Injectable Suspension Prescribing Information" Aug. 2018.
Lilly USA, LLC, "Gemzar(R) (gemitabine) for injection Prescribing Information" May 2019.
Hospira Inc., "Drug Label for Paclitaxel Injection, USP" Feb. 2012.
Villanueva, E. F., et, al., "Nab-Paclitaxel plus gemcitabine in patients with metastatic pancreatic adenocarcinoma: experience of use" Farm Hosp. 2015;39(3):181-185.

* cited by examiner

COMBINATION SOLUTION FOR TREATING CHEMOTHERAPY REFRACTORY CANCER

The present application is a national phase application under 35 U.S.C. 371 of the international application PCT/CN2019/110904, filed Oct. 12, 2019 which, in turn, claims the benefit of priority of C.N. Patent Application CN201811195239.3 filed Oct. 12, 2018; the content of which is hereby incorporated herein by reference in its entirety.

TECHNICAL FIELD OF THE INVENTION

The present application refers to a drug combination for treating chemotherapy refractory cancer.

BACKGROUND OF THE INVENTION

Nowadays, Cancer remains a leading cause of death worldwide. Despite people advance in the treatment of certain forms of cancer through surgery, radiotherapy, and chemotherapy, but cancer remains are incurable. Even when an effective treatment is available for a particular cancer, the side effects of such treatment can be severe resulting in an undesirable reduction in a patient's quality of life, and cancer always develop chemo-refractoriness to chemotherapy.

Most conventional chemotherapy agents have significant toxicity and only limited efficacy, particularly for patients with advanced solid tumors. While conventional chemotherapeutic agents kill cancerous cells, they also damage normal human cells. The chemotherapeutic therapeutic index (i.e., a measure of a therapy's ability to discriminate between cancerous and normal cells) of such chemotherapeutic compounds can be quite low. Frequently, a dose of a chemotherapy drug that is effective at killing cancer cells will also kill normal cells, especially those normal cells (such as epithelial cells and cells of the bone marrow) that undergo frequent cell division. When normal cells are affected by the therapy, side effects frequently include hair loss, suppression of hematopoiesis, and nausea. Depending on the general health of a patient, these adverse events can preclude the further administration of chemotherapy, or, at a minimum, subject cancer patients to extremely unpleasant side effects. Even for cancer patients who respond to chemotherapy with tumor regression, cancers often quickly relapse after the initial response to chemotherapy. Such recurrent cancers are often highly resistant or refractory to chemotherapeutics.

cancer stem cells (CSCs (also called, for example, tumor initiating cells, cancer stem-like cells, stem-like cancer cells, highly tumorigenic cells, or super malignant cells) are cancer cells with high stemness (stemness-high cancer cells) are responsible for the rapid tumor recurrence and resistance to further traditional chemotherapy. There is mounting evidence to suggest that CSCs exist in almost all tumor types as a distinct population, and they give rise to the differentiated cells that form the bulk of the tumor mass and phenotypically characterize the disease. CSCs have been demonstrated to be fundamentally responsible for carcinogenesis, cancer metastasis, cancer recurrence, and relapse (e.g., FIG. 1). CSCs are inherently resistant to conventional chemotherapies, which means they are left behind by conventional therapies that kill the bulk of tumor cells, e.g., FIG. 2. As such, the existence of CSCs has several implications in terms of cancer treatment and therapy. These include, for example, disease identification, selective drug targets, prevention of cancer metastasis and recurrence, treatment of cancer refractory to chemotherapy and/or radiotherapy, treatment of cancers inherently resistant to chemotherapy or radiotherapy and development of new strategies in fighting cancer.

STAT3 is a potent transcription regulator that targets a large number of genes involved in cell cycle, cell survival, oncogenesis, tumor invasion, and metastasis, including, but not limited to, BCL-XL, c-MYC, CYCLIN D1, IDO1, PDL1, VEGF, MMP-2, and SURVIVIN (e.g., FIG. 3). The collective expression of these STAT3 responsive genes maintains the sternness of cancer stem cells (CSCs) required for the survival and propagation of cancer stem cells. STAT3 may therefore play a pivotal role in the survival and self-renewal capacity of CSCs across a broad spectrum of cancers. STAT3 has therefore emerged as a promising target for inhibiting cancer stem cells survival and preventing metastasis. An anti-STAT3 agent with activity against CSCs holds great promise for cancer patients (Boman, B. M., et al. J. Clin. Oncol. 2008. 26(17): p. 2795-99).

According to PCT Patent Application WO2009/036059, the compound having formula (I)

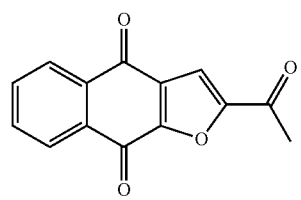

(I)

is an inhibitor of CSCs growth and survival. The compound of formula (I) inhibits STAT3 pathway activity with a cellular $IC_{50}$ of ~0.25 μM. The compound of formula (I) may be synthesized according to PCT Patent Application WO2009/036059, for example, Example 13. In some embodiments, the compound of formula (I) is used in a method of treating cancers. According to PCT Patent Application WO2014/169078, Example 6, the compound of formula (I) was chosen to enter a clinical trial for patients with advanced cancers. According to PCT Patent Application WO2009/036101, the two-drug combination regimen of the compound of formula (I) and another second anticancer agent has a potential synergistic anticancer effect. The development potential of new anti-cancer strategies based on inhibiting the CSCs pathway in preventing cancer metastasis and recurrence, treatment of cancers inherently resistant to chemotherapy and/or radiotherapy, and treatment of cancers inherently resistant to chemotherapy or radiotherapy, there is an urgent need to further develop new, alternative, and more effective new combination therapy regimens based on the compound of formula (I) for specific cancer patients.

Pancreatic cancer is a common type of cancer, it has the characteristics of having rapid disease progression, having poor prognosis for patients, being occult in the early stage of disease, low surgical resection rate, being easy recurrence after surgery, and having low chemotherapy efficiency. At present, surgery is the only possible method to cure. However, more than 80% of patients with metastatic pancreatic cancer have developed locally advanced or metastasized at the time of diagnosis. For a small number of patients who can receive surgical treatment, most of them will eventually develop into advanced pancreatic cancer, with a 5-year survival rate of less than 5% (Hidalgo, 2010). At present, the first-line standard chemotherapy regimens for the patients with unresectable metastatic pancreatic cancer mainly include: FOLFIRINOX (5-fluorouracil (5-FU), leucovorin/LV), irinotecan and oxaliplatin for combined chemotherapy, as for untreated patients, the median overall survival (mOS) is 11.1 months (Conroy, 2011); and the combined chemotherapy regimen of gemcitabine combined with nab-paclitaxel, which was recently completed In the phase II/III trial of MPACT (Von Hoff, 2013), the mOS in the combined group was 8.7 months, and the combined group had an unprecedented 3-year survival rate of 4% (Goldstein, 2014). For patients with disease progression after first-line treatment, currently available treatment options are very limited, for example, for who have not used gemcitabine in the first-line treatment, standard-dose gemcitabine can be used in the second-line treatment; for who have used gemcitabine in the first-line treatment, 5-FU/LV usually be chose in the second-line treatment. The mOS of patients with pancreatic cancer who failed after first-line treatments is about 4 to 5 months. A recent study of Onivyde combined with 5-FU/LV therapeutic regimen shows that for patients with metastatic pancreatic cancer who progressed after gemcitabine-based first-line treatment, the mOS of the combined regimen increased to 6.1 months (Chen, 2015). At present, researchers are still working hard, and there is an urgent need to develop new treatment regimens to improve survival conditions of patients with metastatic pancreatic cancer, especially those with metastatic pancreatic cancer after the failure of first-line treatment.

SUMMARY OF THE INVENTION

Disclosed herein are uses of novel drug combination in the treatment of chemotherapy refractory cancer, the drug combination comprising a therapeutically effective amount of the compound of formula (I)

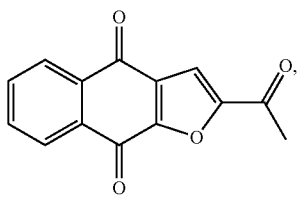

(I)

pharmaceutically acceptable salts or solvates thereof, a low dose of gemcitabine, pharmaceutically acceptable salts or solvates thereof, and a therapeutically effective amount of paclitaxel or pharmaceutically acceptable salts or solvates thereof.

The present disclosure has unexpectedly discovered that in the therapeutic regimen of the compound of formula (I), pharmaceutically acceptable salts or solvates thereof, combined with a low dose of gemcitabine, pharmaceutically acceptable salts or solvates thereof, and paclitaxel, pharmaceutically acceptable salts or solvates thereof, it produces anti-tumor activity and a durable response in patients with metastatic pancreatic cancer whose previous treatments have failed.

In some embodiments, disclosed herein are methods for treating cancer comprising administering to a subject in need thereof a therapeutically effective amount of the compound of formula (I), pharmaceutically acceptable salts or solvates thereof, a low dose of gemcitabine, pharmaceutically acceptable salts or solvates thereof, and a therapeutically effective amount of paclitaxel, pharmaceutically acceptable salts or solvates thereof.

The compound of formula (I), a low dose of gemcitabine, and a paclitaxel can be administered to a patient simultaneously, concurrently, separately, and/or sequentially. Thus, in certain embodiments, the compound of formula (I) and a low dose of gemcitabine are administered to a patient simultaneously, concurrently, separately, and/or sequentially. In certain embodiments, the compound of formula (I) and paclitaxel are administered to a patient simultaneously, concurrently, separately, and/or sequentially.

The compound of formula (I) may be administered in single or divided doses daily. The therapeutically effective amount of the compound of formula (I) is administered daily at a dose of about 80-960 mg, about 80-480 mg. The compound of formula (I) is administered twice a day at a dose of about 80 mg, about 160 mg, or about 240 mg. The paclitaxel can be administered weekly. Wherein paclitaxel can be administered at 10-100 mg/m$^2$ every week. Wherein therapeutically effective amount of paclitaxel is administered weekly at about 80 mg/m$^2$, about 60 mg/m$^2$, and about 40 mg/m$^2$ by infusion. The low dose of gemcitabine can be administered weekly. Wherein low dose of gemcitabine can be administered at 100-800 mg/m$^2$ every week, this dose of gemcitabine is less than 50% of the recommended efficacious dose. Wherein low dose of gemcitabine is administered weekly at about 600 mg/m$^2$, about 550 mg/m$^2$, about 500 mg/m$^2$, about 450 mg/m$^2$, about 400 mg/m$^2$, about 300 mg/m$^2$, about 200 mg/m$^2$ or about 100 mg/m$^2$ by infusion.

In some embodiments, cancers are advanced, metastatic, unresectable, refractory, or recurrent. In some embodiments, the cancer is at least one pancreatic cancer that has progressed after previous treatment. In some embodiments, the pancreatic cancer is pancreatic adenocarcinoma. In some embodiments, the pancreatic cancer is pancreatic ductal adenocarcinoma. In some embodiments, the pancreatic cancer is at least one metastatic pancreatic cancer that has progressed after previous treatment.

In some embodiments, disclosed herein are uses of drug combinations in methods for sensitizing a subject to at least one therapy regimen comprising administering to a subject in need thereof: a therapeutically effective amount of the compound of formula (I), chosen from compounds of formula (I)

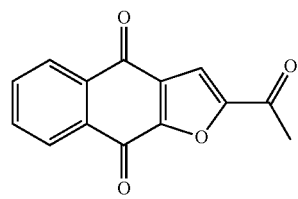

(I)

or pharmaceutically acceptable salts and solvates thereof.

In some embodiments, disclosed herein are methods for sensitizing a subject to at least one therapy regimen comprising administering to a subject in need thereof: a therapeutically effective amount of the compound of formula (I).

In some embodiments, disclosed herein are methods for sensitizing a subject to at least one prior therapy regimen comprising administering to a subject in need thereof: a therapeutically effective amount of the compound of formula (I), chosen from compounds of formula (I)

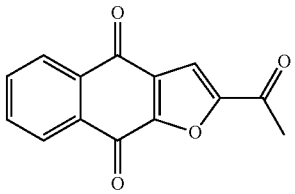
(I)

or pharmaceutically acceptable salts and solvates thereof.

In some embodiments, disclosed herein are uses of drug combinations in methods for sensitizing a subject to at least one prior therapy regimen comprising administering to a subject in need thereof: a therapeutically effective amount of the compound of formula (I).

In some embodiments, disclosed herein are uses of drug combinations in methods for sensitizing a subject to at least one prior therapy regimen comprising administering to a subject in need thereof: a therapeutically effective amount of the compound of formula (I), chosen from compounds of formula (I)

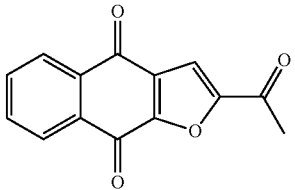
(I)

or pharmaceutically acceptable salts and solvates thereof.

In some embodiments, the at least one prior therapy regimen is chosen from chemotherapy regimens. In some embodiments, the at least one prior therapy regimen is chosen from gemcitabine regimens. In some embodiments, the at least one prior therapy regimen is chosen from gemcitabine-based monotherapy or combination chemotherapy. In some embodiments, the at least one prior therapy regimen is chosen from paclitaxel regimens. In some embodiments, the at least one prior therapy regimen is chosen from FOLFIRINOX, mFOLFIRINOX or Gem-Abraxane (gemcitabine-Albumin paclitaxel) regimens. In some embodiments, the at least one prior therapy regimen is chosen from common therapy regimens for cancers such as surgery, radiotherapy, targeted therapy, and immunotherapy.

In some embodiments, disclosed herein are methods for sensitizing a subject to chemotherapy regimen comprising administering to a subject in need thereof: a therapeutically effective amount of the compound of formula (I), chosen from compounds of formula (I)

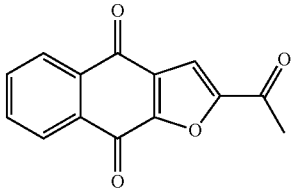
(I)

or pharmaceutically acceptable salts and solvates thereof, a low dose of gemcitabine, and a therapeutically effective amount of paclitaxel. In some embodiments, the subject is a pancreatic cancer patient who has failed a prior therapy. In some embodiments, the subject is a metastatic pancreatic cancer patient who has failed a prior therapy.

In some embodiments, disclosed herein are methods for sensitizing a subject to chemotherapy regimen comprising administering to a subject in need thereof a therapeutically effective amount of the compound of formula (I).

In some embodiments, disclosed herein are uses in methods of inhibiting, reducing, and/or diminishing cancer stem cells and heterogeneous cancer cells survival and/or self-renewal comprising administering to a subject in need thereof a therapeutically effective amount of the compound of formula (I), a low dose of gemcitabine, and a therapeutically effective amount of paclitaxel.

In some embodiments, a kit is disclosed that comprises at least one compound chosen from compounds having formula (I), prodrugs, derivatives, pharmaceutically acceptable salts of any of the foregoing, and solvates of any of the foregoing. In some embodiments, a kit is disclosed that comprises at least one gemcitabine chosen from gemcitabine, prodrugs, derivatives, pharmaceutically acceptable salts of any of the foregoing, and solvates of any of the foregoing. In some embodiments, a kit is disclosed that comprises at least one paclitaxel chosen from paclitaxel, prodrugs, derivatives, pharmaceutically acceptable salts of any of the foregoing, and solvates of any of the foregoing. In some embodiments, a kit is disclosed comprising at least one compound chosen from compounds having formula (I), prodrugs, derivatives, pharmaceutically acceptable salts of any of the foregoing, and solvates of any of the foregoing, at least one gemcitabine chosen from gemcitabine, prodrugs, derivatives, pharmaceutically acceptable salts of any of the foregoing, and solvates of any of the foregoing, and at least one paclitaxel chosen from paclitaxel, prodrugs, derivatives, pharmaceutically acceptable salts of any of the foregoing, and solvates of any of the foregoing.

Aspects and embodiments of the present disclosure are set forth or will be readily apparent from the following detailed description. It is to be understood that both the foregoing general description and the following detailed description are exemplary and explanatory only, and are not intended to be restrictive of the claims.

DETAILED DESCRIPTION OF THE INVENTION

Figure 1:
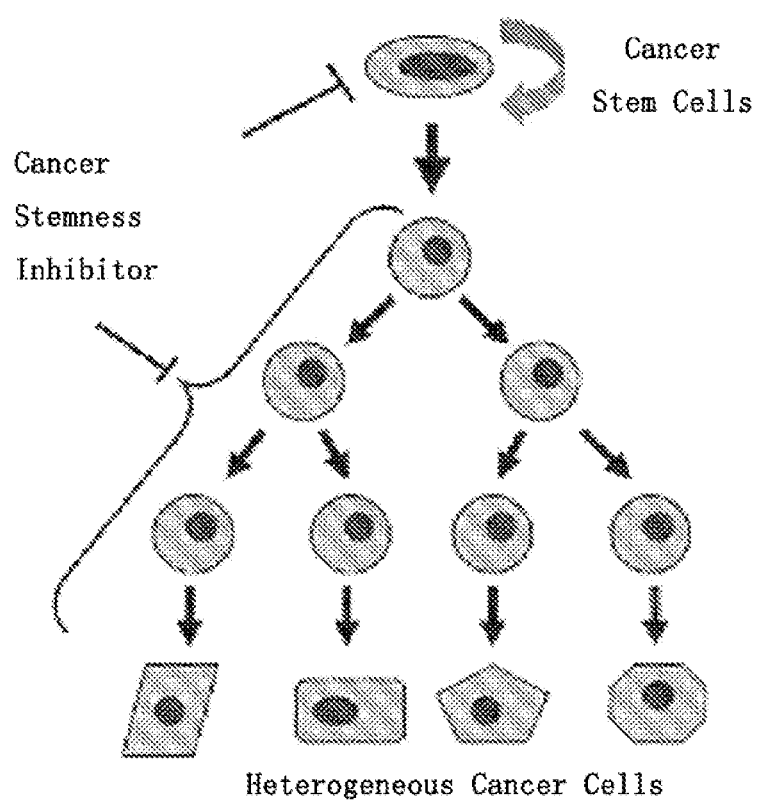
FIG. 1 shows formation of heterogeneous cancer cells from cancer stem cells.

The following are definitions of terms used in the present specification. The initial definition provided for a group or term herein applies to that group or term throughout the present specification individually or as part of another group or term, unless otherwise indicated.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In some embodiments, the term "about" is used to modify a numerical value above and below the stated value by a variance of 10%. In some embodiments, the term "about" is used to modify a numerical value above and below the stated value by a variance of 5%. In some embodiments, the term "about" is used to modify a numerical value above and below the stated value by a variance of 1%. When the term "less than" is used in conjunction with a numerical range, it is intended to cover every optional numerical value and subrange that is less than the range except for the range. For example, "less than 5 mg" is meant to include 1 mg, 2 mg, 3 mg, and 4 mg. In some embodiments, such as be administered less than 600 mg/m$^2$, include be administered 599 mg/m$^2$, be administered at 598 mg/m$^2$, and so on.

The phrase "and/or," as used herein in the present teachings and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. When a range of values is listed herein, it is intended to encompass each value and sub-range within that range. For example, "1-5 mg" is intended to encompass 1 mg, 2 mg, 3 mg, 4 mg, 5 mg, 1-2 mg, 1-3 mg, 1-4 mg, 1-5 mg, 2-3 mg, 2-4 mg, 2-5 mg, 3-4 mg, 3-5 mg, and 4-5 mg.

The terms "administer," "administering," or "administration" are used herein in their broadest sense. These terms refer to any method of introducing to a subject a compound or pharmaceutical composition described herein and can include, for example, introducing the compound systemically, locally, or in situ to the subject. Thus, a compound of the present disclosure produced in a subject from a composition (whether or not it includes the compound) is encompassed in these terms. When these terms are used in connection with the term "systemic" or "systemically," they generally refer to in vivo systemic absorption or accumulation of the compound or composition in the blood stream followed by distribution throughout the entire body.

The term "subject" generally refers to an organism to which a compound or pharmaceutical composition described herein can be administered. A subject can be a mammal or mammalian cell, including a human or human cell. The term also refers to an organism, which includes a cell or a donor or recipient of such cell. In various embodiments, the term "subject" refers to any animal (e.g., a mammal), including, but not limited to humans, mammals and non-mammals, such as non-human primates, mice, rabbits, sheep, dogs, cats, horses, cows, chickens, amphibians, reptiles, fish, nematode, and insects, which is to be the recipient of a compound or pharmaceutical composition described herein. Under some circumstances, the terms "subject" and "patient" are used interchangeably herein in reference to a human subject.

The term "therapeutically effective amount" as used herein refers to its meaning as is generally accepted in the art. The term generally refers to the amount of the compound or composition that will elicit the requisite biological or medical response in a cell, tissue, system, animal or human. For example, if a given clinical treatment is considered effective when there is at least about a 25% reduction in a measurable parameter associated with a disease or disorder, a therapeutically effective amount of a drug for the treatment of that disease or disorder is that amount necessary to effect at least about a 25% reduction in that parameter.

A "therapeutically effective amount" in reference to the treatment of cancer, means an amount capable of invoking one or more of the following effects: (1) inhibition, to some extent, of cancer or tumor growth, including slowing down growth or complete growth arrest; (2) reduction in the number of cancer or tumor cells; (3) reduction in tumor size; (4) inhibition (i.e., reduction, slowing down, or complete stopping) of cancer or tumor cell infiltration into peripheral organs; (5) inhibition (i.e., reduction, slowing down, or complete stopping) of metastasis; (6) enhancement of anti-tumor immune response, which may, but is not required to, result in the regression or rejection of the tumor, or (7) relief, to some extent, of one or more measurable symptoms associated with the cancer or tumor. In some embodiments, the "therapeutically effective amount" refers to the amount that is administered systemically, locally, or in situ (e.g., the amount of compound that is produced in situ in a subject). The therapeutically effective amount may vary according to factors such as the disease state, age, sex, and weight of the individual and the ability of one or more anti-cancer agents to elicit a desired response in the individual. A "therapeutically effective amount" is also one in which any toxic or detrimental effects are outweighed by the therapeutically beneficial effects.

Terms such as "treating", "treatment", "to treat", "alleviating," or "to alleviate" as used herein refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder ("preventing" or "to prevent"). Thus those in need of treatment include those already with the disorder; those prone to have the disorder; and those in whom the disorder is to be prevented.

The term "treating cancer", "treatment of cancer" or an equivalent thereof means to decrease, reduce, or inhibit the replication of cancer cells; decrease, reduce, or inhibit the spread (formation of metastases) of cancer; decrease tumor size; decrease the number of tumors (i.e. reduce tumor burden); lessen or reduce the number of cancerous cells in the body; prevent recurrence of cancer after surgical removal or other anti-cancer therapies; and/or ameliorate measurable treatment endpoints (i.e., outcomes).

The term "standard treatment" as used herein is a term recognized in the art, and is understood to refer to a cancer treatment method widely used in clinical practice, usually be referred to chemotherapy for the treatment of cancer can be combined with surgery and/or radiotherapy. The specific regimens can be found in those websites maintained such as by the National Cancer Institute (www.cancer.gov), the American Society for Clinical Oncology (www.asco.org) and the National Comprehensive Cancer Network (www.nccn.org). In some embodiments, the term "first-line treatment" or "first-line therapy" is a term recognized in the art and is understood to refer to the initial treatment of a disease, which is usually a part of standard treatment regimens, such as surgical treatment followed by chemotherapy and radiotherapy are used as the best treatment, and also are called primary treatment or primary therapy. In some embodiments, the term "second-line treatment" or "second-line therapy" is a term recognized in the art and is understood to refer to chemotherapy treatments given when the initial or primary treatment (first-line or primary therapy) does not work or stops working, it can also be combined with surgery, radiotherapy and/or immunotherapy. As used herein, the term "prior treatment" may include all treatments that patients received before receiving the treatment regimen of the present invention for the present disease, include but not be limited to, first-line treatment, second-line treatment, third-line treatment, etc.

The term "synergy", "synergistic", "synergistically" or "enhanced" as used herein refers to an effect of interaction or combination of two or more components to produce a combined effect greater than the sum of their separate effects (or "additive effects").

The term "cancer" refers to the presence of cells possessing characteristics typical of cancer-causing cells, such as uncontrolled proliferation, immortality, metastatic potential, rapid growth and proliferation rate, and certain morphological features. Often, cancer cells will be in the form of a tumor or mass, but such cells may exist alone within a subject, or may circulate in the blood stream as independent cells, such as leukemic or lymphoma cells.

The term "cancer" comprises, for example, AIDS-related cancers, breast cancers, cancers of the digestive/gastrointestinal tract, endocrine and neuroendocrine cancers, cancers of the eye, genitourinary cancers, germ cell cancers, gynecologic cancers, head and neck cancers, hematologic cancers, musculoskeletal cancers, neurologic cancers, respiratory/thoracic cancers, skin cancers, childhood cancers as well as cancers of unknown primary.

Exemplary AIDS-related cancers include, but are not limited to, AIDS-Related Lymphoma, Primary Central Nervous System Lymphoma and Kaposi Sarcoma.

Exemplary cancers of the digestive/gastrointestinal tract include, but are not limited to, anal cancer, cancer of the anal region, appendix cancer, gastrointestinal carcinoid tumor, bile duct cancer, carcinoid tumor, gastrointestinal cancer, colon cancer, esophageal cancer, gallbladder cancer, gastrointestinal stromal tumors (GIST), islet cell tumors, pancreatic neuroendocrine tumors, liver cancer, pancreatic cancer, rectal cancer, colorectal adenocarcinoma, small intestine cancer, gastroesophageal junction (GEJ) cancer, gastric adenocarcinoma and stomach (gastric) cancer.

Exemplary endocrine and neuroendocrine cancers include, but are not limited to, adrenocortical carcinomas, gastrointestinal carcinoid tumors, islet cell tumors, pancreatic neuroendocrine tumors, adrenocortical carcinoma, Merkel cell carcinomas, non-small cell lung neuroendocrine tumors, small cell lung neuroendocrine tumors, parathyroid cancers, pheochromocytomas, pituitary tumors, and thyroid cancers.

Exemplary genitourinary cancers include, but are not limited to, bladder cancer, kidney (renal cell) cancer, penile cancer, prostate cancer, renal pelvis and ureter cancer, transitional cell, testicular cancer, urethral cancer, Wilms tumor and other childhood kidney tumors.

Exemplary gynecologic cancers include, but are not limited to, cervical cancer, endometrial cancer, uterine cancer, fallopian tube cancer, gestational trophoblastic tumor, ovarian epithelial cancer, ovarian germ cell tumor, ovarian low malignant potential tumor, primary peritoneal cancer, uterine sarcoma, vaginal cancer and vulvar cancer.

Exemplary head and neck cancers include, but are not limited to, hypopharyngeal cancer, laryngeal cancer, lip and oral cavity cancer, metastatic squamous neck cancer with occult primary, mouth cancer, nasopharyngeal cancer, oral cavity cancer, lip and oropharyngeal cancer, paranasal sinus and nasal cavity cancer, parathyroid cancer, pharyngeal cancer, salivary gland cancer, throat cancer and thyroid cancer.

Exemplary hematologic cancers include, but are not limited to, leukemias, acute lymphoblastic leukemia, adult, childhood acute lymphoblastic leukemia, adult acute myeloid leukemia, childhood acute myeloid leukemia, chronic lymphocytic leukemia, chronic myelogenous leukemia, hairy cell leukemia, lymphomas, AIDS-related lymphoma, cutaneous T-cell lymphoma, adult Hodgkin lymphoma, childhood Hodgkin lymphoma, Hodgkin lymphoma during pregnancy, mycosis fungoides, childhood Non-Hodgkin lymphoma, adult Non-Hodgkin lymphoma, Non-Hodgkin lymphoma during pregnancy, primary central nervous system lymphoma, Sezary syndrome, cutaneous T-cell lymphoma, Waldenstrom macroglobulinaemia, chronic myeloproliferative neoplasms, Langerhans cell histiocytosis, multiple myeloma/plasma cell neoplasm, myelodysplastic syndromes and myelodysplastic/myeloproliferative neoplasms.

Exemplary musculoskeletal cancers include, but are not limited to, bone cancer, Ewing's sarcoma, osteosarcoma, malignant fibrous histiocytoma of bone, childhood rhabdomyosarcoma, chondrosarcoma and soft tissue sarcoma.

Exemplary neurologic cancers include, but are not limited to, adult brain tumor, childhood brain tumor, astrocytomas, brain and spinal cord tumors, brain stem glioma, glioblastoma multiforme, atypical teratoid/rhabdoid central nervous system tumor, embryonal central nervous system tumors, germ cell central nervous system tumors, astrocytomas, ependymoma, schwannomas, medulloblastomas, meningiomas craniopharyngioma, neuroblastoma, pituitary tumor, pituitary adenomas and primary central nervous system (CNS) lymphoma.

Exemplary respiratory/thoracic cancers include, but are not limited to, non-small cell lung cancer, small cell lung cancer, malignant mesothelioma, thymoma and thymic carcinoma.

Exemplary skin cancers include, but are not limited to, cutaneous T-cell lymphoma, Kaposi sarcoma, melanoma, Merkel cell carcinoma, skin cancer, cutaneous T-cell lymphoma, mycosis fungoides, intraocular melanoma and Sezary syndrome.

Cancers include refractory versions of any of the above cancers, or a combination of one or more of the above cancers. Some of the exemplified cancers are included in general terms and are included in this term. For example, urological cancer, a general term, includes bladder cancer, prostate cancer, kidney cancer, testicular cancer, and the like; and hepatobiliary cancer, another general term, includes liver cancers (itself a general term that includes hepatocellular carcinoma or cholangiocarcinoma), gallbladder cancer, biliary cancer, or pancreatic cancer. Both urological cancer and hepatobiliary cancer are contemplated by the present disclosure and included in the term "cancer."

Also included within the term "cancer" is "solid tumor", as used herein, the term "solid tumor" refers to those conditions, such as cancer, that form an abnormal tumor mass, such as sarcomas, carcinomas, and lymphomas. Examples of solid tumors include, but are not limited to, non-small cell lung cancer (NSCLC), neuroendocrine tumors, thyomas, fibrous tumors, metastatic colorectal cancer (mCRC), and the like. In some embodiments, the solid tumor disease is an adenocarcinoma, squamous cell carcinoma, large cell carcinoma, and the like.

In some embodiments, the cancer is chosen from pancreatic adenocarcinoma, gastric adenocarcinoma, gastroesophageal junction (GEJ) adenocarcinoma, gastroesophageal adenocarcinoma, non-small cell lung cancer (NSCLC), breast cancer, triple-negative breast cancer (TNBC; i.e., breast cancer that tests negative for estrogen receptors (ER−), progesterone receptors (PR−), and HER2 (Receptor tyrosine-protein kinase erbB-2, also known as CD340 (cluster of differentiation 340), proto-oncogene Neu, ERBB2 (human); HER2−)), ovarian cancer, platinum-resistant ovarian cancer (PROC), melanoma, small cell lung cancer, and cholangiocarcinoma. In some embodiments, the cancer is pancreatic adenocarcinoma. In some embodiments, the cancer is pancreatic ductal adenocarcinoma.

Exemplary pancreatic neuroendocrine tumors (pancreatic NETs or PNETs) include, but are not limited to, gastrinomas (Zollinger-Ellison Syndrome), glucagonomas, isulinomas, somatostatinomas, VIPomas (Verner-Morrison Syndrome), Watery Diarrhea and Hypokalemia Achlorhydria (WDHA) Syndrome, nonfunctional islet cell tumors and multiple endocrine neoplasias type-1 (MEN1; also known as Werner Syndrome).

Exemplary pancreatic exocrine tumors include, but are not limited to, adenocarcinomas, pancreatic ductal adenocarcinomas (PDAC), acinar cell carcinomas, intraductal papillary-mucinous neoplasms (IPMN), mucinous cystadenocarcinomas, solid pseudopapillary neoplasms and pancreatoblastomas.

In some embodiments, each of the cancers is unresectable, advanced, refractory, recurrent, or metastatic.

The terms "progress", "progressed" and "progression" as used herein refer to at least one of the following: (1) a response to prior therapy (e.g., chemotherapy) of progressive disease (PD); (2) the appearance of one or more new lesions after treatment with prior therapy (e.g., chemotherapy); and (3) at least a 5% (e.g., 10%, 20%) increase in the sum of diameters of target lesions, taking as a reference the smallest sum on study (this includes the baseline sum if that is the smallest on study); and (4) The non-target lesions are clearly progressing.

As used herein, the term "sensitizing" or equivalents thereof (e.g., "sensitize" or "sensitization") means making subjects that were previously resistant, non-responsive, or somewhat responsive to a therapy regimen (e.g., traditional chemotherapy, targeted therapy, or immunotherapy) sensitive, responsive, or more responsive to that therapy regimen. In certain embodiments, the term "sensitizing" or equivalents thereof includes "resensitizing" or equivalents thereof, making subjects that became resistant, non-responsive, or somewhat responsive to a therapy regimen (e.g., traditional chemotherapy, targeted therapy, or immunotherapy) because of prior exposure to such therapy regimen sensitive, responsive, or more responsive to that therapy regimen.

As used herein, the term "at least one compound of formula (I)" means a compound chosen from compounds having formula (I)

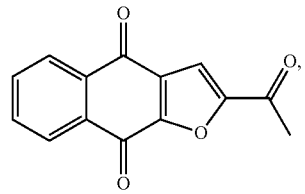

prodrugs, derivatives, pharmaceutically acceptable salts of any of the foregoing, and solvates of any of the foregoing. The term "compound of formula (I)" means a compound chosen from compounds having formula (I)

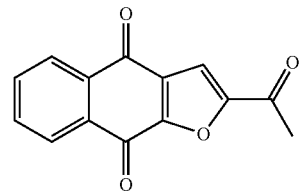

or pharmaceutically acceptable salts of any of the foregoing and solvates of any of the foregoing.

In some embodiments, prodrugs or derivatives of compounds having formula (I) are STAT3 inhibitors. Non-limiting examples of prodrugs of compounds having formula (I) are the phosphoric ester and phosphoric diester described in PCT patent application WO2009/036099 as compound numbers 4011 and 4012 and also suitable compounds described in U.S. Pat. No. 9,150,530. Non-limiting examples of derivatives of compounds having formula (I) include the derivatives disclosed in PCT patent application WO2009/036059. The disclosures of PCT patent applications WO2009/036099, WO2009/036059 and U.S. Pat. No. 9,150,530 are hereby incorporated herein by reference in their entireties for any purpose.

The compound having formula (I), shown below,

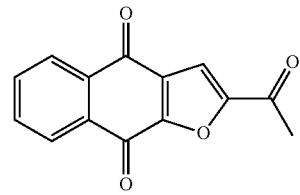

may also be known as 2-acetylnaphtho[2,3-b]furan-4,9-dione, napabucasin and include tautomers thereof.

Suitable methods of preparing 2-acetylnaphtho[2,3-b]furan-4,9-dione (including its crystalline forms and additional cancer stemness inhibitors) are described in PCT patent applications WO2009/036099, WO2009/036101, WO2011/116398, WO2011/116399, and WO2014/169078; the content of each application is hereby incorporated herein by reference in its entirety for any purpose.

As used herein, the term "at least one gemcitabine" means a compound chosen from gemcitabine, prodrugs, derivatives, pharmaceutically acceptable salt of any of the foregoing, and solvates of any of the foregoing. In certain embodiments, the term "gemcitabine" means a compound chosen from gemcitabine, pharmaceutically acceptable salts and solvates thereof.

As used herein, the term "at least one paclitaxel" means a compound chosen from paclitaxel, prodrugs, derivatives, pharmaceutically acceptable salts of any of the foregoing, and solvates of any of the foregoing. In certain embodiments, the term "paclitaxel" means a compound chosen from paclitaxel, pharmaceutically acceptable salts and solvates thereof. In some embodiments, the "paclitaxel" refers to a paclitaxel injection approved for production by China Food and Drug Administration (now by National Medical Products Administration).

As used herein, the "compound of formula (I)", "paclitaxel", and "gemcitabine" contained in the term "drug combination" can either be mixed together to form a single administration unit, or they can form administration units separately, these active ingredients can be used simultaneously, sequentially, consecutively, and separately.

The term "salt(s)", as used herein, includes acidic and/or basic salts formed with inorganic and/or organic acids and bases. As used herein, the term "pharmaceutically acceptable salt" refers to those salts which are, within the scope of sound medical judgment, suitable for use in contact with the tissues of subjects without undue toxicity, irritation, allergic response and/or the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19.

Pharmaceutically acceptable salts may be formed with inorganic or organic acids. Non-limiting examples of suitable inorganic acids include hydrochloric acid, hydrobromic acid, phosphoric acid, sulfuric acid, and perchloric acid. Non-limiting examples of suitable organic acids include acetic acid, oxalic acid, maleic acid, tartaric acid, citric acid, succinic acid, and malonic acid. Other non-limiting examples of suitable pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid.

Salts may be prepared in situ during the isolation and purification of the disclosed compound, or separately, such as by reacting the compound with a suitable base or acid, respectively. Non-limiting examples of pharmaceutically acceptable salts derived from bases include alkali metal, alkaline earth metal, ammonium and $N^+(C_{1-4}alkyl)_4$ salts. Non-limiting examples of suitable alkali or alkaline earth metal salts include sodium, lithium, potassium, calcium, magnesium, iron, zinc, copper, manganese, and aluminum salts. Further non-limiting examples of suitable pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Non-limiting examples of suitable organic bases from which salts may be derived include primary amines, secondary amines, tertiary amines, substituted amines including naturally occurring substituted amines, cyclic amines, and basic ion exchange resins, such as isopropylamine, trimethylamine, diethylamine, triethylamine, tripropylamine, and ethanolamine. In some embodiments, pharmaceutically acceptable base addition salts can be chosen from ammonium, potassium, sodium, calcium, and magnesium salts.

The term "solvate" represents an aggregate that comprises one or more molecules of a compound of the present disclosure with one or more molecules of a solvent or solvents. Solvates of the compounds of the present disclosure include, for example, hydrates.

The term "low dose" as used herein refers to a therapeutically effective amount whose dose is lower than the standard therapeutic dose, for example, the recommended standard dose of gemcitabine is 1000 to 1200 mg/m². In some embodiments, the low dose of gemcitabine is less than about 800 mg/m², about 600 mg/m², about 550 mg/m², about 500 mg/m², about 450 mg/m², about 400 mg/m², about 350 mg/m², about 300 mg/m², about 250 mg/m², about 200 mg/m², about 150 mg/m² or about 100 mg/m² is administered weekly. In some embodiments, the low dose of gemcitabine is less than 50% of the recommended efficacious dose or even low.

In some embodiments, gemcitabine and paclitaxel are administered according to a regimen on days 1, 8, and 15 of every 28 day cycle. In some embodiments, low dose of gemcitabine (e.g., about 600 mg/m², about 550 mg/m², about 500 mg/m², about 450 mg/m², about 400 mg/m², about 350 mg/m², about 300 mg/m², about 250 mg/m², about 200 mg/m², about 150 mg/m² or about 100 mg/m²) is administered weekly. In some embodiments, low dose of gemcitabine (e.g., about 600 mg/m², about 550 mg/m², about 500 mg/m², about 450 mg/m², about 400 mg/m², about 350 mg/m², about 300 mg/m², about 250 mg/m², about 200 mg/m², about 150 mg/m² or about 100 mg/m²) is administered weekly up to 7 weeks. In some embodiments, low dose of gemcitabine (e.g., about 600 mg/m², about 550 mg/m², about 500 mg/m², about 450 mg/m², about 400 mg/m², about 350 mg/m², about 300 mg/m², about 250 mg/m², about 200 mg/m², about 150 mg/m² or about 100 mg/m²) is administered weekly for 3 out of every 4 weeks. In some embodiments, low dose of gemcitabine 100 to 800 mg/m² is administered weekly, preferred 100 to 600 mg/m². In some embodiments, low dose of gemcitabine about 800 mg/m², about 600 mg/m², about 300 mg/m², or about 100 mg/m². In some embodiments, low dose of gemcitabine less than about 600 mg/m² is administered weekly. In some embodiments, paclitaxel about 100 about mg/m², 80 mg/m², about 70 mg/m², about 60 mg/m², about 50 mg/m², about 40 mg/m², about 30 mg/m², about 20 mg/m², or about 10 mg/m² is administered weekly. In some embodiments, paclitaxel about 100 mg/m², about 80 mg/m², about 70 mg/m², about 60 mg/m², about 50 mg/m², about 40 mg/m², about 30 mg/m², about 20 mg/m², or about 10 mg/m² is administered weekly up to 7 weeks. In some embodiments, paclitaxel about 100 mg/m², about 80 mg/m², about 70 mg/m², about 60 mg/m², about 50 mg/m², about 40 mg/m², about 30 mg/m², about 20 mg/m², or about 10 mg/m² is administered weekly for 3 out of every 4 weeks. In some embodiments, paclitaxel 10 to 100 mg/m$^2$ is administered weekly, preferred 40 to 80 mg/m$^2$. In some embodiments, paclitaxel about 80 mg/m$^2$, about 60 mg/m$^2$, or about 40 mg/m$^2$ is administered weekly. In some embodiments, paclitaxel less than 80 mg/m$^2$ is administered weekly. In some embodiments, paclitaxel is administered intravenously at 80 mg/m$^2$ according to the regimen, start at least 2 hours after taking the compound of formula (I) on the same day, and the infusion duration is about 60 minutes. In some embodiments, gemcitabine is administered intravenously at 600 mg/m$^2$ immediately after paclitaxel infusion according to the regimen for the duration is about 30 to 60 minutes.

In some embodiments, the compound of formula (I) may be administered in a total daily dose ranging from about 80 mg to about 960 mg. In some embodiments, the compound of formula (I) may be administered in a total daily dose ranging from about 80 mg to about 480 mg. In some embodiments, the compound of formula (I) may be administered in a total daily dose ranging from about 160 mg to about 480 mg. In some embodiments, the total amount of the compound of formula (I) is administered once daily. In some embodiments, the compound of formula (I) is administered in a dose of about 480 mg. In some embodiments, the compound of formula (I) is administered in a dose of about 400 mg. In some embodiments, the compound of formula (I) is administered in a dose of about 320 mg. In some embodiments, the compound of formula (I) is administered in a dose of about 240 mg. In some embodiments, the compound of formula (I) is administered in a dose of about 160 mg. In some embodiments, the total amount of the compound of formula (I) is administered in divided doses (more than once) daily, such as twice daily (BID) or more often. In some embodiments, the compound of formula (I) may be administered in a total daily dose ranging from about 80 mg to about 480 mg twice daily. In some embodiments, the compound of formula (I) may be administered in a total daily dose ranging from about 80 mg to about 240 mg twice daily. In some embodiments, the compound of formula (I) is administered in a total daily dose of about 240 mg twice daily. In some embodiments, the compound of formula (I) is administered in a total daily dose of about 480 mg twice daily. In some embodiments, the compound of formula (I) is administered in a total daily dose of about 160 mg twice daily. In some embodiments, the compound of formula (I) is administered in a total daily dose of about 80 mg twice daily. In some embodiments, the compound of formula (I) is administered at about 240 mg, twice a day, with intervals of 8 to 12 hours. In some embodiments, the compound of formula (I) is administered at about 80 mg, twice a day, with intervals of 8 to 12 hours.

The compound disclosed herein may be in the form of a pharmaceutical composition (a pharmaceutic preparation). In some embodiments, the pharmaceutical compositions (pharmaceutic preparations) may comprise the compound of formula (I) and at least one pharmaceutically acceptable carrier. In some embodiments, the pharmaceutical compositions (pharmaceutic preparations) may comprise compound of formula (I), paclitaxel and a low dose of gemcitabine. In some embodiments, the pharmaceutical compositions (pharmaceutic preparations) may comprise compound of formula (I) and paclitaxel. In some embodiments, the pharmaceutical compositions (pharmaceutic preparations) may comprise compound of formula (I) and a low dose of gemcitabine.

The term "carrier" as used herein means a pharmaceutically acceptable material, composition or vehicle, such as, for example, a liquid or solid filler, diluent, excipient, solvent or encapsulating material involved in or capable of carrying or transporting the subject pharmaceutical compound from one organ, or portion of the body, to another organ, or portion of the body. Each carrier must be "acceptable" in the sense of being compatible with the other ingredients of the formulation and not injurious to the patient. Non-limiting examples of pharmaceutically acceptable carriers and/or diluents include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers, and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

Pharmaceutical compositions (pharmaceutic preparations) disclosed herein that are suitable for oral administration may be in the form of capsules, cachets, pills, tablets, lozenges (using a flavored basis, usually sucrose and acacia or tragacanth), powders, granules, a solution in an aqueous or non-aqueous liquid, a suspension in an aqueous or non-aqueous liquid, an oil-in-water emulsion, a water-in-oil emulsion, an elixir, a syrup, pastilles (using an inert base, such as gelatin, glycerin, sucrose, and/or acacia) and/or mouthwashes, each containing a predetermined amount of the compound of the present disclosure.

A pharmaceutical composition (a pharmaceutic preparation) disclosed herein may be administered as a bolus, electuary, or paste.

Solid dosage forms for oral administration (capsules, tablets, pills, dragees, powders, granules and the like) may be mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type also may be employed as fillers in soft and hard-filled gelatin capsules using such excipients as lactose or milk sugars, as well as high molecular weight polyethylene glycols and the like.

Liquid dosage forms for oral administration may include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-p-cyclodextrin, may be used to solubilize compounds.

The pharmaceutical compositions (pharmaceutic preparations) also may include adjuvants such as wetting agents, emulsifying and suspending agents, sweetening, flavoring, coloring, perfuming and preservative agents. Suspensions, in addition to the compounds according to the disclosure, may contain suspending agents as, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions (pharmaceutic preparations) disclosed herein, for rectal or vaginal administration may be presented as a suppository, which may be prepared by mixing one or more compounds according to the present disclosure, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the compounds of the present disclosure. Pharmaceutical compositions which are suitable for vaginal administration also may include pessaries, tampons, creams, gels, pastes, foams or spray formulations containing carriers that are known in the art to be appropriate.

Dosage forms for the topical or transdermal administration of a pharmaceutical composition (a pharmaceutic preparation) or pharmaceutical tablet of the present disclosure may include powders, sprays, ointments, pastes, creams, lotions, gels, solutions, patches and inhalants. The pharmaceutical composition or pharmaceutical tablet may be mixed under sterile conditions with a pharmaceutically acceptable carrier, and with any preservatives, buffers, or propellants which may be required.

The ointments, pastes, creams and gels may contain, in addition to the pharmaceutical composition (pharmaceutic preparation) or pharmaceutical tablet of the present disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a pharmaceutical composition (pharmaceutical preparation) or a pharmaceutical tablet of the present disclosure, excipients such as lactose, talc, silicic acid, aluminum hydroxide, calcium silicates and polyamide powder, or mixtures of these substances. Additionally, sprays may contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of the present disclosure.

Compositions (pharmaceutic preparations) suitable for parenteral administration may comprise at least one more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In various embodiments, a compound of formula (I) described herein is contained in pharmaceutical compositions. Said pharmaceutical compositions (pharmaceutic preparations) include compounds of formula (I), pharmaceutically acceptable salts and solvates thereof, and one or more surfactants. In some embodiments, the surfactant is sodium lauryl sulfate (SLS), sodium dodecyl sulfate (SDS), or one or more polyoxylglycerides. For example, the polyoxyglyceride can be lauroyl polyoxylglycerides (sometimes referred to as Gelucire™) or linoleoyl polyoxylglycerides (sometimes referred to as Labrafil™). Examples of such compositions are shown in PCT Patent Application No. WO2014/169078, contents of which are incorporated herein in its entirety.

At least four properties of CSCs are believed to contribute to malignancy: stemness, dysregulation of stemness signaling pathways, a resistance to traditional cancer therapies and a propensity to metastasize. As used herein, "stemness" generally means the capacity for a stem cell population to self-renew and transform into cancer stem cells (Gupta P B et al., Nat. Med. 2009; 15(9): 1010-1012). While CSCs form only a small percentage of the total cancer cell population in a tumor (Clarke M F, Biol. Blood Marrow Transplant. 2009; 1 1 (2 suppl. 2): 14-16), they give rise to heterogeneous lineages of differentiated cancer cells that make up the bulk of the tumor (see Gupta et al. 2009). In addition, CSCs possess the ability to spread to other sites in the body by metastasis where they seed the growth of new tumors (Jordan C T et al. N. Engl. J. Med. 2006; 355(12): 1253-1261).

The induction and maintenance of stemness properties in CSCs is fueled by a progressive dysregulation of stemness signaling pathways including, but not limited to, those signaling pathways associated with Janus kinase/signal transducers and activators of transcription (JAK/STAT), Hedgehog (Desert (DHH), Indian (IHH), and Sonic (SHH))/PATCHED/(PTCH1)/SMOOTHENED (SMO), NOTCH/DELTA-LIKE (DLL1, DLL3, DLL4)/JAGGED (JAG1, JAG2)/CSL (CBF1/Su(H)/Lag-1), WNT/APC/GSK3/p-CATENIN/TCF4 and NANOG (Boman B M et al., J. Clin. Oncol. 2008; 26(17):2828-2838).

It is the aberrant regulation of these stemness signaling pathways in CSCs (see Boman et al. 2008) that is presumed to confer resistance to chemotherapy and radiation treatment in CSCs which eventually leads to the relapse and spread of the cancer. Thus, while chemotherapy and radiation kills the majority of rapidly dividing bulk cancer cells in a tumor, dysregulation of stemness signaling pathways in CSCs may enable CSCs to avoid chemotherapy induced cell death and also explain how the surviving CSCs acquire the ability to metastasize to sites in the body that are distant from the primary tumor.

Figure 3:
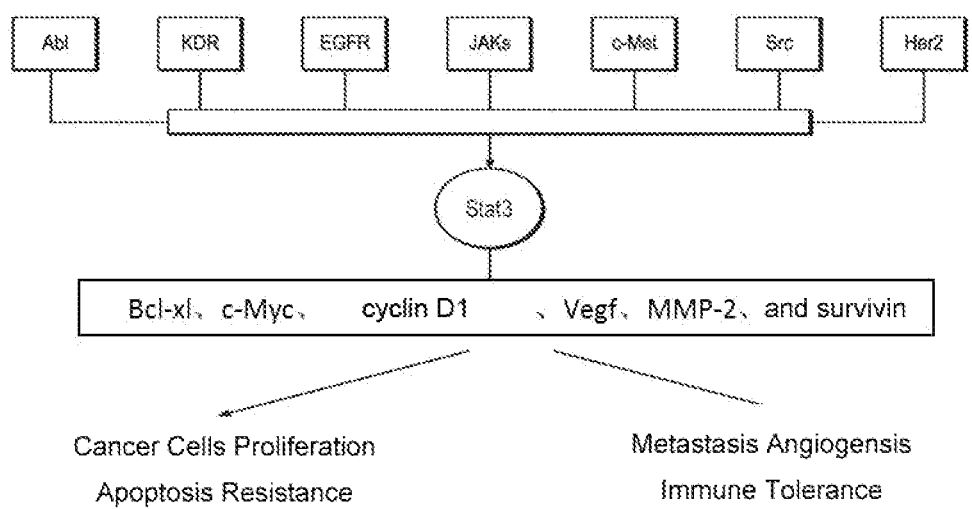
FIG. 3 shows the STAT3 pathway in cancer.

The Signal Transducer and Activator of Transcription 3 (also known as Acute-Phase Response Factor, APRF, DNA-Binding Protein APRF, ADMIO 3, HIES; referred to herein as STAT3) that function at the junction of several cytokine-signaling pathways. e.g., FIG. 3. Catlett-Falcone, R., et al. Immunity, 1999. 10(1): p. 105-15; Bromberg, J. F., et al.

Cell, 1999. 98(3): p. 295-303; Kanda, N., et al. Oncogene, 2004. 23(28): p. 4921-29; Schlette, E. J., et al. J Clin Oncol, 2004. 22(9): p. 1682-88; Niu, G., et al. Oncogene, 2002. 21(13): p. 2000-08; Xie, T. X., et al. Oncogene, 2004. 23(20): p. 3550-60). STAT3 not only regulate the expression of genes controlling cell cycle (CYCLIN D1, D2, and c-MYC), cell survival (BCL-XL, BCL-2, MCL-1), and angiogenesis (HIF1α, VEGF) (Furqan et al. Journal of Hematology & Oncology (2013) 6:90), but is also a key negative regulator of tumor immune surveillance and immune cell recruitment. (Kortylewski, M., et al. Nat. Med., 2005. 11(12): p. 1314-21; Burdelya, L., et al. J. Immunol., 2005. 174(7): p. 3925-31; and Wang, T., et al. Nat. Med., 2004. 10(1): p. 48-54).

In normal cells, STAT3 activation is transient and tightly regulated, lasting for example, from about 30 minutes to a few hours. However, in a wide variety of human cancers, including all of the major carcinomas as well as some hematologic tumors, STAT3 is found to be aberrantly active (Lin et al., Oncogene (2000) 19, 2496-2504; Bromberg J. Clin. Invest. (2002) 109: 1 139-1 142; Buettner et al., Clinical Cancer Research (2002) 8, 945-954; Frank Cancer Letters 251 (2007) 199-21 OYu et al. Nature Reviews Cancer (2004) 4, 97-105). Persistently active STAT3 is present in more than half of all breast and lung cancers as well as colorectal cancers (CRC), ovarian cancers, hepatocellular carcinomas, multiple myelomas, pancreatic cancer and in more than 95% of all head/neck cancers.

Abrogation of STAT3 signaling using anti-sense oligonucleotides, siRNA, dominant-negative form of STAT3, and/or the targeted inhibition of STAT3 dependent tyrosine kinase activity causes cancer cell-growth arrest, apoptosis, and reduction of metastasis frequency both in vitro and/or in vivo suggesting CSCs stemness is reliant on the constitutive activation of the STAT3 transcription factor. (Pedranzini, L, et al. J Clin. Invest., 2004. 1 14(5): p. 619-22; Bromberg, J. F., et al. Cell, 1999. 98(3): p. 295-303; Darnell, J. E. Nat. Med., 2005. 1 1 (6): p. 595-96; and Zhang, L, et al. Cancer Res, 2007. 67(12): p. 5859-64.) STAT3 may therefore play a pivotal role in the survival and self-renewal capacity of CSCs across a broad spectrum of cancers.

As noted above, the methods disclosed herein may treat at least one disorder related to aberrant STAT3 pathway activity in a subject. Aberrant STAT3 pathway activity can be identified by expression of phosphorylated STAT3 ("pSTAT3"), or its surrogate upstream or downstream regulators or through the detection of pSTAT3 localized to the nucleus.

The STAT3 pathway can be activated in response to cytokines, for example, IL-6, or by one or more tyrosine kinases, for example, EGFR, JAKs, ABL, KDR, c-MET, SRC, and HER2. See, e.g., FIG. 3. The downstream effectors of STAT3 include, but are not limited to, BCL-XL, c-MYC, CYCLIND1, VEGF, MMP-2, and SURVIVIN. Id. The STAT3 pathway has been found to be aberrantly active in a wide variety of cancers. Persistently active STAT3 pathway may occur in more than half of breast and lung cancers, hepatocellular carcinomas, multiple myelomas and in more than 95% of head and neck cancers. Blocking the STAT3 pathway causes cancer cell-growth arrest, apoptosis, and reduction of metastasis frequency in vitro and/or in vivo. Activated STAT3 has also been demonstrated in a number of autoimmune and inflammatory diseases. Furthermore, as interleukin-6 mediated inflammation has been disclosed to be the common causative origin for Atherosclerosis, Peripheral Vascular Disease, Coronary Artery Disease, hypertension, Osteroprorosis, Type 2 Diabetes, and Dementia, and as gp130-JAKS-STATs has been disclosed to be the main pathway activated by IL-6, inhibition of the STAT3 pathway may treat or prevent these diseases as well. (Libby, P., et al. Circulation, 2002. 105(9): p. 1 135-43; Stephens, J. W., et al. Mol. Genet. Metab., 2004. 82(2): p. 180-86; Cesari, M., et al. Circulation, 2003. 108(19): p. 2317-22; Orshal, J. M. and R. A. Khalil. Am. J. Physiol. Regul. Integr. Comp. Physiol., 2004. 286(6): p. R1013-23; Manolagas, S. C. Bone, 1995. 17(2 Suppl): p. 63S-67S; and Yaffe, K., et al. Neurology, 2003. 61 (1): p. 76-80).

In some embodiments, the at least one disorder may be chosen from cancers having aberrant STAT3 pathway activity. For example, activated pSTAT3 has been detected in pancreatic cancer cells (Wei et al. Oncogene (2003) 22(3): 319-329; Scholz et al. Gastroenterology (2003) 125:891-905; Toyonaga et al. Cancer Lett. (2003) 10; 201 (1):107-16; Qiu et al. Cancer Sci. (2007) 98(7): 1099-106).

In some embodiments, the at least one disorder may be chosen from autoimmune diseases related to aberrant STAT3 pathway activity and inflammatory diseases related to aberrant STAT3 pathway activity. In some embodiments, the diseases related to aberrant STAT3 pathway activity may be chosen from inflammatory bowel diseases, arthritis, Crohn's diseases, ulcerative colitis, rheumatoid arthritis, asthma, allergy, and systemic lupus erythematosus.

In some embodiments, the at least one disorder may be chosen from CNS diseases related to aberrant STAT3 pathway activity. In some embodiments, the CNS diseases may be chosen from autoimmune demyelination disorders, Alzheimer's, strokes, ischemia reperfusion injuries, and multiple sclerosis. In some embodiments, the at least one disorder is chosen from diseases caused by inflammation and related to aberrant STAT3 pathway activity. In some embodiments, the diseases caused by inflammation and related aberrant STAT3 pathway activity may be chosen from peripheral vascular disease, coronary artery disease, hypertension, osteoporosis, type 2 diabetes, and dementia.

As discussed above, CSCs are a sub-population of cancer cells (found within solid tumors or hematological cancers) that possess characteristics normally associated with stem cells. These cells can grow faster after reduction of non-stem regular cancer cells by chemotherapy, which may be the mechanism responsible for the frequent relapse of cancer after chemotherapies. In contrast to the bulk of cancer cells, which are non-tumorigenic, CSCs are tumorigenic (tumor-forming). In human acute myeloid leukemia, the frequency of these cells is less than 1 in 10,000. Bonnet, D. and J. E. Dick. Nat. Med., 1997. 3(7): p. 730-37.

Figure 2:
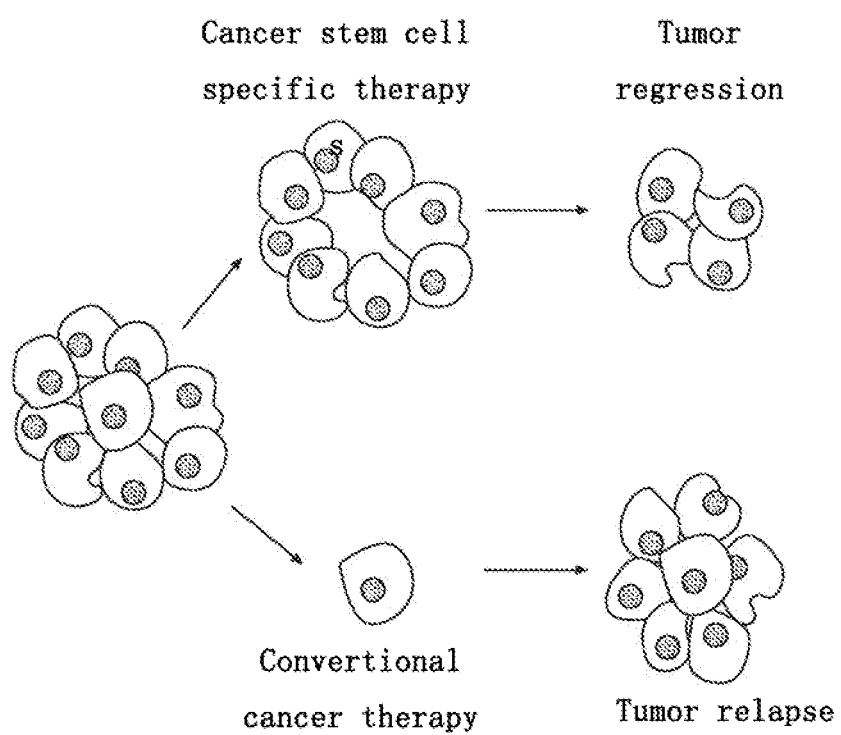
FIG. 2 shows the cancer stem cells specific and conventional cancer therapies.

The efficacy of cancer treatments are, in the initial stages of testing, often measured by the amount and the size of tumor mass they kill off. As CSCs form a very small proportion of the tumor cell population and have markedly different biologic characteristics than their differentiated progeny, the measurement of tumor mass may not select for drugs that act specifically on the stem cells. In fact, CSCs are radioresistant and refractory to chemotherapeutic and targeted drugs. Normal human somatic stem cells are naturally resistant to chemotherapeutic agents-they have various pumps (e.g., multidrug resistance protein pump) that efflux drugs, higher DNA repair capability, and have a slow rate of cell turnover (chemotherapeutic agents naturally target rapidly replicating cells). CSCs, being the mutated counterparts of normal stem cells, may also have similar functions that allow them to survive therapy. In other words, conventional chemotherapies kill differentiated (or differentiating) cells, which form the bulk of the tumor that is unable to generate new cells. e.g., FIG. 2. A population of CSCs that gave rise to the tumor could remain untouched and cause a relapse of the disease. Furthermore, treatment with chemotherapeutic agents may only leave chemotherapy-resistant CSCs, increasing the likelihood that the ensuing tumor is also resistant to chemotherapy. Moreover, cancer stem cells have also been demonstrated to be resistant to radiation therapy (XRT). Hambardzumyan, et al. Cancer Cell, 2006. 10(6): p. 454-56; and Baumann, M., et al. Nat. Rev. Cancer, 2008. 8(7): p. 545-54.

Since surviving CSCs can repopulate the tumor and cause relapse, anticancer therapies that include strategies against CSCs hold great promise. Jones R J et al., J Natl Cancer Inst. 2004; 96(8):583-585. By CSCs targeting pathways, it may be possible to treat patients with aggressive, non-resectable tumors and refractory or recurrent cancers as well as prevent tumor metastasis and recurrence. Development of specific therapies targeting CSCs pathways. Therefore, it is expected to extend the survival period and improve the quality of life of cancer patients, especially those patients suffering from metastatic disease.

Recent studies have disclosed cancer stem cells able to regenerate tumors (e.g., FIG. 1). These cancer stem cells are disclosed to be functionally linked with continued malignant growth, cancer metastasis, recurrence, and cancer drug resistance. Cancer stem cells and their differentiated progeny appear to have markedly different biologic characteristics. They persist in tumors as a distinct, but rare population. Conventional cancer drug screenings depend on measurement of the amount of tumor mass and, therefore, may not identify drugs that act specifically on the stem cells. In fact, cancer stem cells have been disclosed to be resistant to standard chemotherapies and are enriched after standard chemotherapy treatments, see, e.g., FIG. 2, which can result in refractory cancer and recurrence. Cancer stem cells have also been demonstrated to be resistant to radiotherapy. Baumann, M., et al. Nat. Rev. Cancer, 2008. 8(7): p. 545-54. The reported cancer types in which cancer stem cells have been isolated include breast cancer, head cancer, neck cancer, lung cancer, ovarian cancer, pancreatic cancer, colorectal carcinoma, prostate cancer, melanoma, multiple myeloma, Kaposi sarcoma, Ewing's sarcoma, liver cancer, medulloblastoma, brain tumors, and leukemia. STAT3 has been identified as a cancer stem cells survival and self-renewal factor. Therefore, STAT3 inhibitors may kill cancer stem cells and/or may inhibit cancer stem cells self-renewal. According to some embodiments, cancer stem cells or cancer stem cells refer to a minute population of cancer stem cells that have self-renewal capability and are tumorigenic. In previous studies, it has been proved that the compound of formula (I) can effectively inhibit STAT3 pathways, thereby inhibit the growth and survival of CSCs. In clinical trials, the compound of formula (I) can be used to treat patients with advanced cancer. Based on previous experiments, the present invention unexpectedly discovered that new types of pharmaceutical compositions of the compound of formula (I), a low dose of gemcitabine and paclitaxel can also effectively treat patients with advanced cancer, especially patients with metastatic pancreatic cancer after failure of previous treatment. Before this, it has never been reported that a combination chemotherapy regimen containing low-dose gemcitabine and paclitaxel can be effectively used in the treatment of patients with advanced pancreatic cancer. Therefore, the present invention provides a new option for improving the survival of patients with metastatic pancreatic cancer in advanced stages, especially after failure of first-line treatment.

Disclosed herein are methods of inhibiting, reducing, and/or diminishing cancer stem cells survival and/or self-renewal, comprising administering a therapeutically effective pharmaceutical compositions, that include the compound of formula (I) combined with a low dose of gemcitabine. Disclosed herein are methods of inhibiting, reducing, and/or diminishing cancer stem cells survival and/or self-renewal, comprising administering a therapeutically effective amount of the compound of formula (I) combined with a therapeutically effective amount of paclitaxel. Also disclosed herein are methods of inhibiting, reducing, and/or diminishing cancer stem cells survival and/or self-renewal, comprising administering a therapeutically effective amount of the compound of formula (I) combined with a low dose of gemcitabine and a therapeutically effective amount of paclitaxel. In some embodiments, the compound of formula (I) is included in a pharmaceutical composition.

Disclosed herein are methods of treating at least one cancer that is refractory to conventional chemotherapies and/or targeted therapies in a subject, comprising administering a therapeutically effective amount of the compound of formula (I) combined with a low dose of gemcitabine. Disclosed herein are methods of treating at least one cancer that is refractory to conventional chemotherapies and/or targeted therapies in a subject, comprising administering a therapeutically effective amount of the compound of formula (I) combined with a therapeutically effective amount or a low dose of paclitaxel weekly. Disclosed herein are methods of treating at least one cancer that is refractory to conventional chemotherapies and/or targeted therapies in a subject, comprising administering a therapeutically effective amount of the compound of formula (I) combined with a low dose of gemcitabine and a therapeutically effective amount of paclitaxel weekly. In various embodiments, the compound of formula (I) is included in a pharmaceutical composition.

Disclosed herein are methods of treating or preventing cancer relapse or metastasis in a subject, comprising administering a therapeutically effective amount of the compound of formula (I) combined with a low dose of gemcitabine. Also disclosed herein are methods of treating or preventing cancer relapse or metastasis in a subject, comprising administering a therapeutically effective amount of the compound of formula (I) combined with a therapeutically effective amount or a low dose of paclitaxel weekly. Also disclosed herein are methods of treating or preventing cancer relapse or metastasis in a subject, comprising administering a therapeutically effective amount of the compound of formula (I) combined with a low dose of gemcitabine and a therapeutically effective amount or a low dose of paclitaxel weekly. In various embodiments, the compound of formula (I) is included in a pharmaceutical composition. In various embodiments, the subject is a pancreatic cancer patient who has failed a previous treatment. In various embodiments, the subject is a patient with metastatic pancreatic cancer after failure of previous treatment.

Disclosed herein are methods of treating cancer in a subject, comprising administering a therapeutically effective amount of the compound of formula (I) combined with a low dose of gemcitabine. Disclosed herein are methods of treating cancer in a subject, comprising administering a therapeutically effective amount of the compound of formula (I) combined with a therapeutically effective amount or a low dose of paclitaxel weekly. Disclosed herein are methods of treating cancer in a subject, comprising administering a therapeutically effective amount of the compound of formula (I) combined with a low dose of gemcitabine and a therapeutically effective amount or a low dose of paclitaxel weekly. In various embodiments, the compound of formula (I) is included in a pharmaceutical composition.

Disclosed herein are uses of pharmaceutical compositions in methods for treating cancer in a subject, the composition comprising a therapeutically effective amount of the compound of formula (I), a low dose of gemcitabine and a therapeutically effective amount or low dose of paclitaxel weekly. The compound of formula (I) is administered daily at a dose of 80 to 960 mg. The paclitaxel can be administered at 10-100 mg/m² weekly. The gemcitabine can be administered at 100-800 mg/m² weekly. In some preferred embodiments, the compound of formula (I) is administered in a total daily dose ranging from about 80 mg to about 480 mg. In some preferred embodiments, the paclitaxel is administered at 40 to 80 mg/m² weekly. In some preferred embodiments, the gemcitabine is administered at 100 to 600 mg/m² weekly. In some embodiments, the subject is a pancreatic cancer patient who has failed a previous treatment. In various embodiments, the subject is a patient with metastatic pancreatic cancer after failure of previous treatment.

In some embodiments, each of the cancers may be unresectable, advanced, refractory, recurrent, or metastatic. In some embodiments, the cancer may be pancreatic cancer. In some embodiments, the cancer may be pancreatic cancer that has progressed after previous treatment. In some embodiments, the pancreatic cancer may be pancreatic adenocarcinoma. In some embodiments, the pancreatic cancer may be pancreatic ductal adenocarcinoma. In some embodiments, the cancer may be metastatic pancreatic cancer. In some embodiments, the cancer is metastatic pancreatic cancer that has progressed after previous treatment. In some embodiments, the cancer may be associated with overexpression of activated pSTAT3. In some embodiments, the cancer may be associated nuclear β-catenin localization.

EXAMPLES

Examples are provided below to further illustrate different features of the present disclosure. The examples also illustrate useful methodology for practicing the invention. These examples do not limit the claimed invention.

The methods disclosed herein comprise administering to a subject in need thereof comprising a low dose of gemcitabine, paclitaxel weekly, and the compound of formula (I).

Example 1

Figure 4:
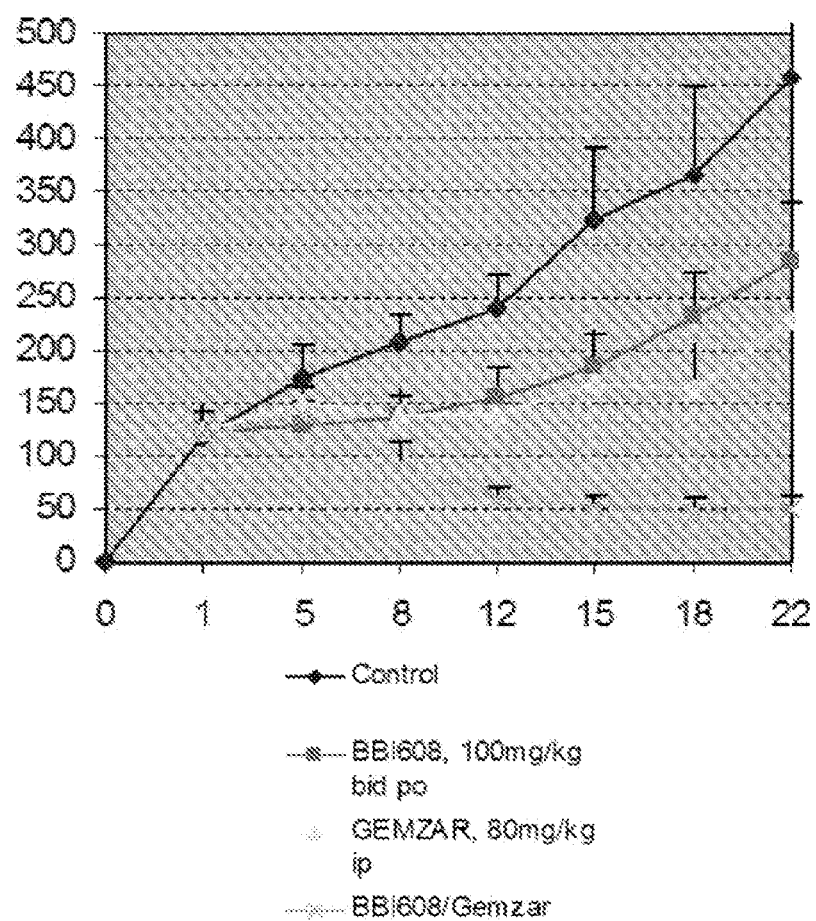
FIG. 4 show an exemplary effect of 2-acetylnaphtho[2,3-b]furan-4,9-dione, gemcitabine (Gemzar), and the combination of 2-acetylnaphtho[2,3-b]furan-4,9-dione and gemcitabine treatment on tumor volume in an xenograft tumor mouse model according to certain embodiments of the present disclosure.

The effects of 2-acetylnaphtho[2,3-b]furan-4,9-dione, the compound of formula (I), gemcitabine, and a combination of 2-acetylnaphtho[2,3-b]furan-4,9-dione and gemcitabine were studied. Specifically, immunosuppressed mice with established human pancreatic adenocarcinoma (Panc-1) were treated with vehicle control, 2-acetylnaphtho[2,3-b]furan-4,9-dione (100 mg/kg, PO, bid), gemcitabine (Gemzar, 80 mg/kg, IV, q3d), or the combination of 2-acetylnaphtho[2,3-b]furan-4,9-dione and gemcitabine. Tumor size was evaluated periodically during treatment. Each point represents the mean±SEM of five tumors. As shown in FIG. 4, while 2-acetylnaphtho[2,3-b]furan-4,9-dione or gemcitabine showed certain effects in inhibiting tumor growth, the combination significantly reduced tumor growth in the mouse model.

Example 2

Detection of the effects of 2-acetylnaphtho[2,3-b]furan-4,9-dione with or without paclitaxel on cancer stem cells for cancer stem cell markers in cancer xenograft animal models.

Human cancer cells were implanted subcutaneously into the right abdomen of 5 to 7 weeks athymic nude mice. When the tumor size reaches 200 mm³, administer 2-acetylnaphtho[2,3-b]furan-4,9-dione (for example, 50 mg/kg (BID) by oral gavage (n=3/group)), paclitaxel, or 2-acetylnaphtho[2,3-b]furan-4,9-dione combined with paclitaxel to treat animals. Tumors were collected 24 hours after the first dose.

The harvested tissues were fixed in 3.7% neutral buffered formaldehyde at 4° C. overnight. Paraffin embedding were performed. Cut those into approximately 5 microns and fix them on positively charged glass slides. After baking and deparaffinization, the slides with tumor or control tissue were incubated in 10 mM sodium citrate (pH 6.0) for 10 minutes. After antigen retrieval, use primary antibody P-STAT3 (Rabbit, Cell Signaling, 1:100), β-catenin (Mouse, Santa Cruz, 1:400) to label slides overnight at 4° C., and then use Alexa Fluor Fluorescent dye-conjugated secondary antibody (1:500, Invitrogen). After mounting, the glass slides containing DAPI (Invitrogen) with Prolong mounting medium were detected under the 20× objective lens of a Zeiss fluorescence microscope, and analyzed with Zen software.

Figure 5:
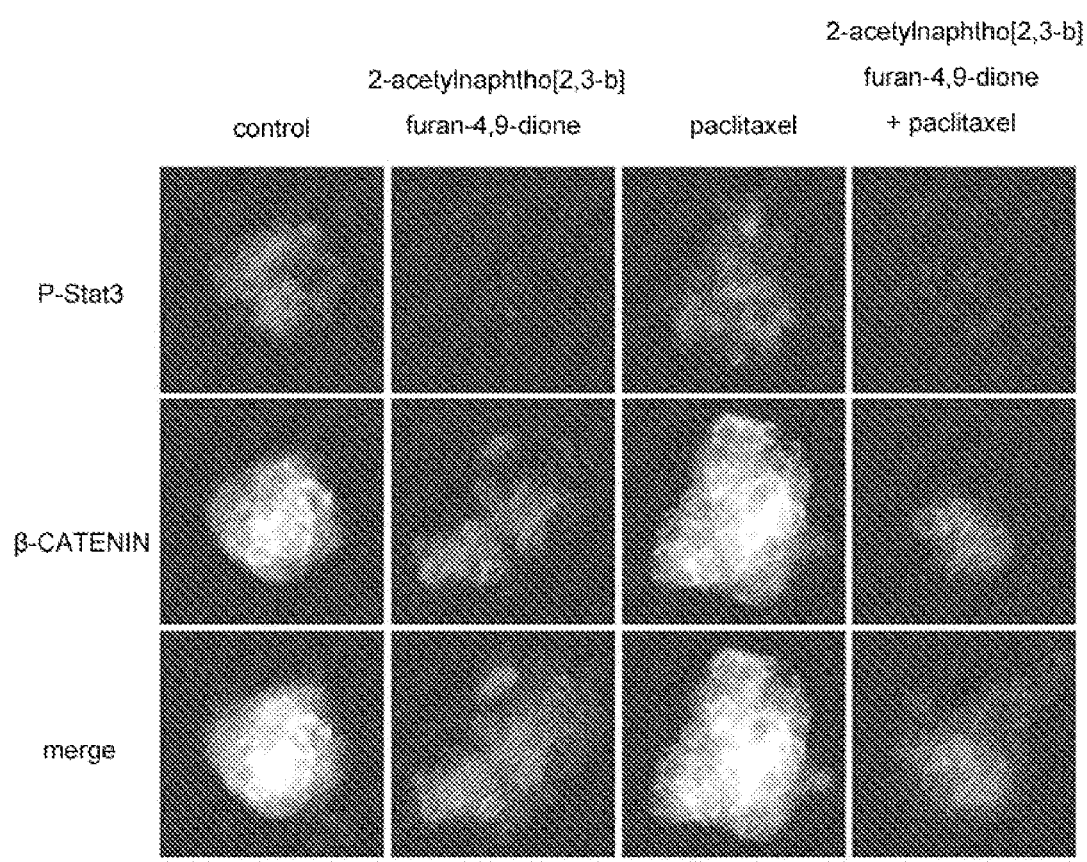
FIG. 5 shows an exemplary effect of 2-acetylnaphtho[2,3-b]furan-4,9-dione, paclitaxel, and 2-acetylnaphtho[2,3-b]furan-4,9-dione combined with paclitaxel treatment on cancer stemness markers p-Stat3 and β-catenin levels in pancreatic cancer stem cells (Panc-1) in vitro.

As shown in FIG. 5, paclitaxel alone can lead to increased staining of stem cell markers, and 2-acetylnaphtho[2,3-b]furan-4,9-dione alone can significantly reduce the expression of stem cell markers p-STAT3 and β-catenin, when 2-acetylnaphtho[2,3-b]furan-4,9-dione is combined with paclitaxel, the expression of stem cell markers drops to a lower level.

Example 3

In a phase II/III extended open label international multicenter experiment, search the effect of the compound of formula (I), 2-acetylnaphtho[2,3-b]furan-4,9-dioen combined with paclitaxel and a low dose of gemcitabine on patients with advanced pancreatic cancer who have failed previous treatments.

In the clinical study, we observed the anti-tumor activity and safety of 2-acetylnaphtho[2,3-b]furan-4,9-dione combined with paclitaxel weekly and a low dose of gemcitabine in patients with advanced pancreatic cancer who failed previous treatment. There are imaging disease progressions in patients who have received at least first-line systemic treatment in the past and failed. Previous treatments include gemcitabine-based single-agent or combination chemotherapy, and/or FOLFIRINOX/mFOLFIRINOX chemotherapy.

Patients enrolled in every 4 weeks (28 days) as a treatment cycle, received 2-acetylnaphtho[2,3-b]furan-4,9-dione 240 mg orally, twice a day (the total daily dose is 480 mg), combined with paclitaxel and a low dose of gemcitabine treatment, on the first day of the first treatment cycle start with paclitaxel at 80 mg/m² IV was given, and then gemcitabine was given at 600 mg/m² IV administering on the first, eighth, and fifteenth days of every 28-day treatment cycle, once a drug toxicity occurs, the dose can be adjusted (reduce or stop).

The remission and progression of the tumor were evaluated according to the RECIST 1.1 standard. To evaluate the antitumor activity of 2-acetylnaphtho[2,3-b]furan-4,9-dione combined with paclitaxel and a low dose of gemcitabine.

Among the patients enrolled with advanced pancreatic cancer, 1 patient had received third-line chemotherapy (first-line gemcitabine+Tegafur; second-line gemcitabine; third-line Avelumab) and disease progression occurred before enrollment, after enrollment treatment, the target lesion was reduced by 9.1% in the first evaluation (8 weeks after randomization into the experiment), RECIST: SD (stable disease), the target lesion was reduced by 41% in the second evaluation (20 weeks after randomization into the experiment), RECIST reached PR (partial response), and the non-target lesions were significantly reduced; 1 patient had received first-line chemotherapy (capecitabine+Tegafur) and disease progression occurred before enrollment, after enrollment treatment, the target lesions shrank by 25.6% in the first evaluation (8 weeks after randomization into the experiment), RECIST: SD, and the non-target lesions reduced significantly. Two patients are still undergoing the regimen treatment currently.

Adverse events related to 2-acetylnaphtho[2,3-b]furan-4, 9-dione observed in all patients receiving treatment were mainly gastrointestinal adverse events (Such as diarrhea, constipation, nausea, vomiting, etc.), the combined medication regimen did not increase the patient's side effects and has good safety.

This experiment shows that 2-acetylnaphtho[2,3-b]furan-4,9-dione combined with paclitaxel and a low dose of gemcitabine have a good synergistic effect, in patients with metastatic pancreatic cancer who had failed in previous treatment, 2-acetylnaphtho[2,3-b]furan-4,9-dione (240 mg BID) combined with paclitaxel at 80 mg/m² IV weekly and gemcitabine at 600 mg/m² IV is safe, tolerable, and has good anti-tumor activity.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described accordingly, all suitable modifications and equivalents may be resorted to, falling within the scope of the present disclosure.

Unless defined otherwise, all technical and scientific terms used herein have the same meaning as commonly understood by one of ordinary on to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

The invention claimed is:
1. A method for treatment of pancreatic cancer in a patient, said method comprising administering to said patient a combinatorial pharmaceutical composition, the combinatorial pharmaceutical composition comprising a therapeutically effective amount of the compound of formula (I):

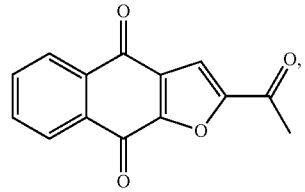

(I)

or pharmaceutically acceptable salts and solvates thereof,
a low dose of gemcitabine or pharmaceutically acceptable salts and solvates thereof, and
a weekly dose of therapeutically effective amount of paclitaxel in an IV injectable formulation that is not nab-paclitaxel,
wherein, the therapeutically effective amount of the compound of formula (I) or pharmaceutically acceptable salts and solvates thereof is administered at a dose of about 80 mg to about 960 mg per day, the low dose of gemcitabine or pharmaceutically acceptable salts and solvates thereof is administered at a dose of about 100 mg/m² to about 600 mg/m² by infusion per week, the therapeutically effective amount of paclitaxel is administered at a dose of about 10 mg/m² to about 80 mg/m² by infusion per week, and
wherein the pancreatic cancer is refractory to conventional chemotherapy, at least one targeted cancer therapy, or both.

2. The method according to claim 1, wherein the pancreatic cancer is selected from the group consisting of advanced pancreatic cancer, metastatic pancreatic cancer, unresectable pancreatic cancer, refractory pancreatic cancer and recurrent chemo-resistant pancreatic cancer.

3. The method according to claim 1, wherein the patient is a pancreatic cancer patient who has failed in at least one prior cancer therapy for pancreatic cancer.

4. The method according to claim 3, wherein the at least one prior cancer therapy comprises a first-line systemic treatment, wherein the systemic treatment is a chemotherapy regimen selected from the group consisting of a gemcitabine-based monotherapy, gemcitabine-based combination chemotherapy, FOLFIRINOX or mFOLFIRINOX-based therapy and Gem-Abraxane (gemcitabine-Albumin paclitaxel) regimens.

5. The method according to claim 3, wherein the at least one prior cancer therapy is selected from the group consisting of a first-line treatment, a second-line treatment, and a third-line treatment.

6. The method according to claim 1, wherein the compound of formula (I), the low dose of gemcitabine, and paclitaxel are administered to the patient simultaneously, separately, and/or sequentially.

7. The method according to claim 1, wherein the compound of formula (I) is administered in multiple separate doses.

8. The method according to claim 1, wherein the compound of formula (I) is administered at a dose of about 240 mg twice daily.

9. The method according to claim 1, wherein the gemcitabine is administered as infusion on days 1, 8, and 15 of every 28-day cycle at a dose selected from the group consisting of about 600 mg/m², about 550 mg/m², about 500 mg/m², about 450 mg/m², about 400 mg/m², about 300 mg/m², about 200 mg/m², and about 100 mg/m².

10. The method according to claim 1, wherein the paclitaxel is administered as infusion on days 1, 8, and 15 of every 28-day cycle at a dose selected from the group consisting of about 80 mg/m², about 70 mg/m²f, about 60 mg/m², about 50 mg/m², about 40 mg/m², about 30 mg/m², about 20 mg/m², and about 10 mg/m².

11. The method according to claim 1, wherein the gemcitabine is administered weekly for 3 out of every 4 weeks.

12. The method according to claim 1, wherein the paclitaxel is administered weekly for 3 out of every 4 weeks.

13. A method for sensitizing a patient with pancreatic cancer who has failed in at least one prior therapy for pancreatic cancer, said method comprising administering to said patient a combinatorial pharmaceutical composition, the combinatorial pharmaceutical composition comprising a therapeutically effective amount of the compound of formula (I):

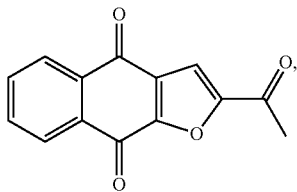

or pharmaceutically acceptable salts and solvates thereof,
a low dose of gemcitabine or pharmaceutically acceptable salts and solvates thereof, and
a weekly dose of therapeutically effective amount of paclitaxel in an IV injectable formulation that is not nab-paclitaxel,
wherein, the therapeutically effective amount of the compound of formula (I) or pharmaceutically acceptable salts and solvates thereof is administered at a dose of about 80 mg to about 960 mg per day, the low dose of gemcitabine or pharmaceutically acceptable salts and solvates thereof is administered at a dose of about 100 mg/m² to about 600 mg/m² by infusion per week, the therapeutically effective amount of paclitaxel is administered at a dose of about 10 mg/m2 to about 80 mg/m2 by infusion per week,
whereby said patient becomes sensitive or responsive to at least one chemotherapy regimen for pancreatic cancer.

14. The method according to claim 13, wherein the pancreatic cancer is selected from the group consisting of advanced pancreatic cancer, metastatic pancreatic cancer, unresectable pancreatic cancer, refractory pancreatic cancer and recurrent chemo-resistant pancreatic cancer.

15. The method according to claim 13, wherein the at least one prior therapy comprises a first-line systemic treatment, wherein the systemic treatment is a chemotherapy regimen selected from the group consisting of a gemcitabine-based monotherapy, gemcitabine-based combination chemotherapy, FOLFIRINOX or mFOLFIRINOX-based therapy and Gem-Abraxane (gemcitabine-Albumin paclitaxel) regimens.

16. The method according to claim 13, wherein the at least one prior cancer therapy is selected from the group consisting of a first-line treatment, a second-line treatment, and a third-line treatment.

17. The method according to claim 13, wherein the compound of formula (I), the low dose of gemcitabine, and paclitaxel are administered to the patient simultaneously, separately, and/or sequentially.

18. The method-according to claim 13, wherein the compound of formula (I) is administered in multiple separate doses.

19. The method according to claim 13, wherein the compound of formula (I) is administered at a dose of about 240 mg twice daily.

20. The method according to claim 13, wherein the gemcitabine is administered as infusion on days 1, 8, and 15 of every 28-day cycle at a dose selected from the group consisting of about 600 mg/m², about 550 mg/m², about 500 mg/m², about 450 mg/m², about 400 mg/m², about 300 mg/m², about 200 mg/m², and about 100 mg/m².

21. The method according to claim 13, wherein the paclitaxel is administered as infusion on days 1, 8, and 15 of every 28-day cycle at a dose selected from the group consisting of about 80 mg/m², about 70 mg/m², about 60 mg/m², about 50 mg/m², about 40 mg/m², about 30 mg/m², about 20 mg/m², and about 10 mg/m².

* * * * *